(12) United States Patent
Willner et al.

(10) Patent No.: US 7,135,295 B1
(45) Date of Patent: Nov. 14, 2006

(54) DETECTION OF SMALL MOLECULES BY USE OF A PIEZOELECTRIC SENSOR

(75) Inventors: Itamar Willner, Mevaseret Zion (IL); Zelig Eshhar, Rehovot (IL)

(73) Assignees: Yissum Research Development Company of the Hebrew University of Jerusalem, Jerusalem (IL); Yeda Research and Development Co. Ltd., Rehovot (IL); Biosensor Applications Sweden AB, Sundbyberg (SE)

(*) Notice: Subject to any disclaimer, the term of this patent is extended or adjusted under 35 U.S.C. 154(b) by 0 days.

(21) Appl. No.: 09/889,936

(22) PCT Filed: Jan. 25, 2000

(86) PCT No.: PCT/IL00/00048

§ 371 (c)(1),
(2), (4) Date: Nov. 19, 2001

(87) PCT Pub. No.: WO00/43774

PCT Pub. Date: Jul. 27, 2000

(30) Foreign Application Priority Data

Jan. 25, 1999 (IL) ................................. 128212

(51) Int. Cl.
*G01N 33/53* (2006.01)

(52) U.S. Cl. .................. 435/7.1; 435/4; 435/70.21; 435/287.2; 427/427; 427/806

(58) Field of Classification Search .............. 23/230; 422/12, 61; 436/527, 806, 518, 512, 53; 423/230; 435/7.1, 70.21, 287.2
See application file for complete search history.

(56) References Cited

U.S. PATENT DOCUMENTS

| | | | |
|---|---|---|---|
| 4,236,893 A | 12/1980 | Rice | |
| 4,242,096 A | 12/1980 | Oliveira et al. | |
| 4,314,821 A * | 2/1982 | Rice | ............................ 436/540 |
| 4,735,906 A | 4/1988 | Bastiaans | |
| 4,999,284 A | 3/1991 | Ward et al. | |
| 5,658,732 A | 8/1997 | Ebersole et al. | |

FOREIGN PATENT DOCUMENTS

| | | |
|---|---|---|
| EP | 0 453 224 | 10/1991 |
| WO | WO 97/04314 | 2/1997 |

(Continued)

OTHER PUBLICATIONS

Lederman et al, A single amino acid substitution in a common african allele of the CD4 molecule ablates binding of the monoclonal antibody, OKT4, 1991, Mol Imm, 28(11), 1171,1181.*

(Continued)

Primary Examiner—Long V. Le
Assistant Examiner—Nelson Yang
(74) Attorney, Agent, or Firm—Browdy and Neimark, PLLC

(57) ABSTRACT

A protein comprising an antigen-binding portion formed by two cooperating peptide sequences of FIGS. 3A and 3B of the application. The protein may alternatively comprise an altered antigen-binding portion where at least one of the peptide sequences is an altered sequence, an altered sequence being a sequence of FIG. 3A or 3B in which one or more of an amino acid residue has been added, deleted or replaced by another amino acid residue. The altered antigen-binding portion retains substantially the same antigen-binding specificity as said antigen-binding portion. Also disclosed are apparatus, systems and methods for detecting small assayed molecules in a sample using the protein.

61 Claims, 29 Drawing Sheets

FOREIGN PATENT DOCUMENTS

WO          WO 98/57141         12/1998

OTHER PUBLICATIONS

Colman, Effects of amino acid sequence changes on antibody-antigen interactions, 1994, Res Imm, 145, 33-36.*

Paul W.E. Fundamental immunology, 3rd Edition, 1993, p. 292-295.*

Rudikoff et al, Single amino acid substitution altering antigen-binding specificity, Proc. Natl. Acad. Sci. USA 1982 vol. 79: pp. 1979-1983.*

Sten-Anders Brink, "Bofors Schnauzer—A Biosensor for Detection of Explosives", *Eurel International Conference: The Detection of Abandoned Land Mines; A Humanitarian Imperative Seeking a Technical Solution*, 1996, p. 33-36.

Upvan Narang et al., "Multianalyte Detection Using a Capillary-Based Flow Immunosensor", *Analytical Biochemistry*, 1998, pp. 13-19, vol. 255, article No. AB72411.

Alan Shons et al, "An Immunospecific Microbalance", *J. Biomed, Mater, Res.*, 1972, pp. 565-570, vol. 6.

Dean D. Fetterolf et al., "An Enzyme-Linked Immunosorbent Assay (ELISA) for Trinitrotoluene (TNT) Residue on Hands", *Journal of Forensic Sciences*, 1991, pp. 343-349, vol. 36, No. 2.

Hiroshi Muramatsu et al., "Piezoelectric Crystal Biosensor System for Detection of *Escherichia coli*", *Analytic Letters*, 1989, pp. 2155-2166, vol. 22(9).

H. Muramatsu et al., "Piezoelectric Immuno Sensor for the Detection of *Candida albicans Microbes*", *Analytica Chimica Acta.*, 1986, pp. 257-261, vol. 188.

Michael D. Ward et al., "In Situ Interfacial Mass Detection with Piezoelectric Transducers", *Science*, 1990, pp. 1000-1007, vol. 249.

Ahmad A. Suleiman et al., "Recent Developments in Piezoelectic Immunosensors: A Review", *Analyst*, 1994, pp. 2279-2282, vol. 119.

Joy E. Roederer et al., "Microgravimetric Immunoassay with Piezoelectric Crystals", *Anal. Chem.*, 1983, pp. 2333-2336, vol. 55.

Hiroshi Muramatsu et al., "Piezoelectric Crystal Biosensor Modified with Protein A for Determination of Immunoglobulins"., *Anal. Chem.*, 1987, pp. 2760-2763, vol. 59.

Jakob Slanina et al., "Determination of Sulfur Dioxide in Ambient Air by a Computer-Controlled Thermodenuder System", *Anal. Chem.*, 1987, pp. 2764-2766, vol. 59.

Bernd König et al., "Detection of Viruses and Bacteria with Piezoelectric Immunosensors", *Analytical Letters*, 1993, pp. 1567-1585, vol. 26(8).

Patent Abstracts of Japan, Publication No. 01269485, Publication date Oct. 26, 1989.

Patent Abstracts of Japan, Publication No. 01269488, Publication date Oct. 26, 1989.

Patent abstracts for DE 3733986, published Apr. 20, 1989.

* cited by examiner

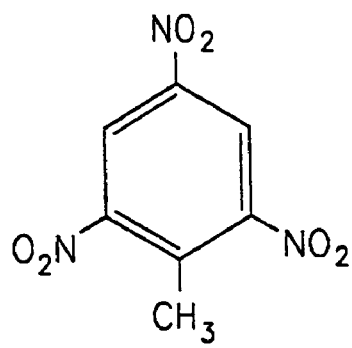
TNT
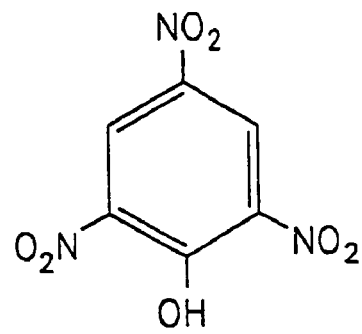
TNP
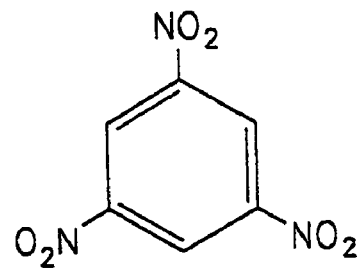
TNB
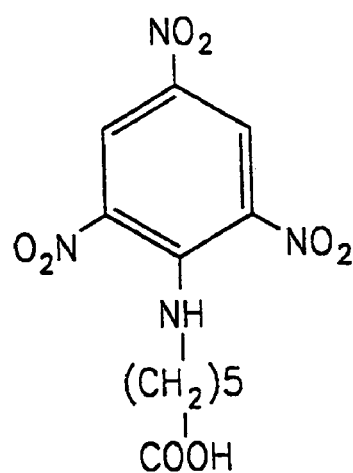
TNP-cap
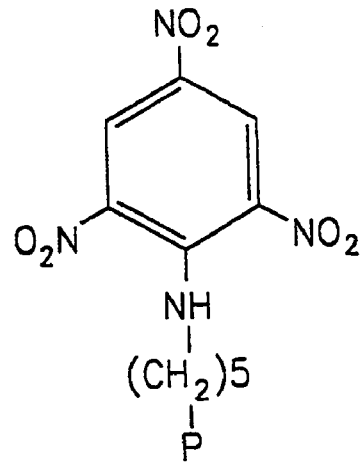
FIG.1A

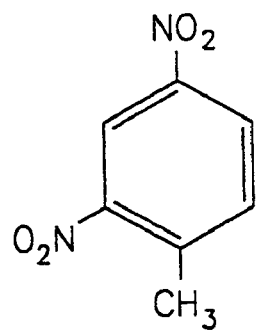
2,4-DNT
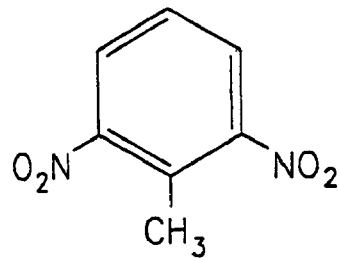
2,6-DNT
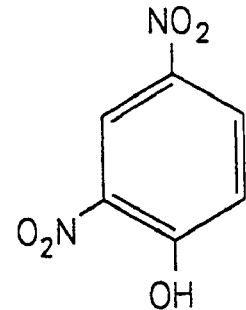
2,4-DNP
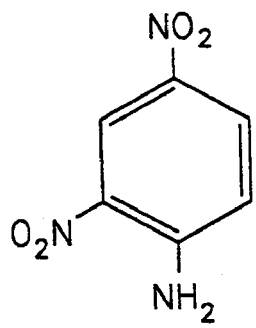
2,4-DNA
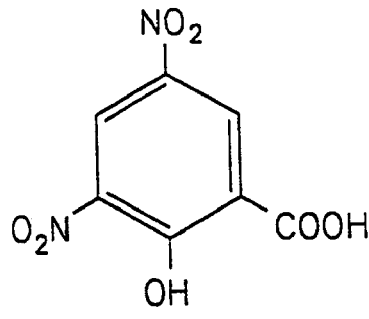
DNS
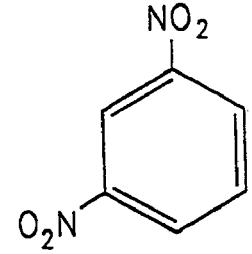
m-DNB
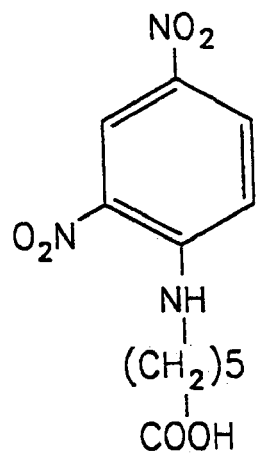
2,4-DNP-cap
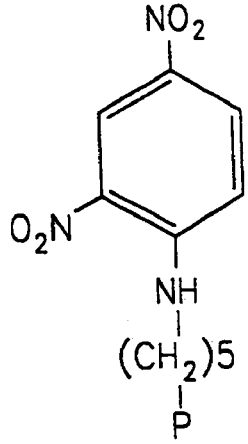
FIG.1B

```
1   ATG AGA GTG CTG ATT CTT TTG TGG CTG TTC ACA GCC TTT CCT GGT ATC CTG TCT GAT GTG  60
    M   R   V   L   I   L   L   W   L   F   T   A   F   P   G   I   L   S   D   V

61  CAG CTT CAG GAG TCG GGA CCT GGC CTG GTG AAG CCT TCC CAG TCT CTG TCC CTC ACC TGC  120
    Q   L   Q   E   S   G   P   G   L   V   K   P   S   Q   S   L   S   L   T   C

121 TCT GTC ACT GGT TAC TCA ATC ACC AGT GGT TAT TGG AAC TGG ATC CGG CAG TTT CCA      180
    S   V   T   G   Y   S   I   T   S   G   Y   W   N   W   I   R   Q   F   P

181 GGA AAC AAA CTG GAG TGG ATG GGC TAC ATA AGC TAC AGT GGT AGC ACT AGC TAC AAC CCA  240
    G   N   K   L   E   W   M   G   Y   I   S   Y   S   G   S   T   S   Y   N   P

241 TCT CTC AGA AGT CGA ATC TCT ATC ACT CGA GAC ACA TCC AAG AAC CAG TTC TTC CTG CAG  300
    S   L   R   S   R   I   S   I   T   R   D   T   S   K   N   Q   F   F   L   Q

301 TTG AAT TCT GTG ACT TCT GAG GAC ACA GCC ACA TAT TAC TGT GCA AGA TGG GAC TAC GGT  360
    L   N   S   V   T   S   E   D   T   A   T   Y   Y   C   A   X   R   W   D   Y   G

361 ACT ACC TAC GGG TAC TTC GAT GTC TGG GGC CAA GGG ACT ACG GTC ACC  408
    T   T   Y   G   Y   F   D   V   W   G   Q   G   T   T   V   T
                                    N3'VH (J1)
```

FIG.3A

```
  1  TCT AGA GGA GAT ATC GTT ATG ACC CAG TCT CCA TCC TCC CTG AGT GTG TCA GCA GGA GAG  60
     S   R   G   D   I   V   M   T   Q   S   P   S   S   L   S   V   S   A   G   E

61  AAG GTC ACT ATG AGC TGC AAG TCC AGT CAG AGT CTG TTA AAC AGT AGA AAT CAA AAG AAC  120
     K   V   T   M   S   C   K   S   S   Q   S   L   L   N   S   R   N   Q   K   N

121  TAC TTG GCC TGG TAC CAG CAG AAA CCA GGA CAG CCT CCT AAA CTT TTG ATC TAC GGG GTA  180
     Y   L   A   W   Y   Q   Q   K   P   G   Q   P   P   K   L   L   I   Y   G   V

181  TTT ATT AGG GAT TCT GGG GTC CCT GAT CGC TTC ACA GGC AGT GGA TCT GGA ACC GAT TTC  240
     F   I   R   D   S   G   V   P   D   R   F   T   G   S   G   S   G   T   D   F

241  ACT CTT ACC ATC AGC AGT GTG CAG GCT GAA GAC CTG GCA GTT TAT TAC TGT CAG AAT GAT  300
     T   L   T   I   S   S   V   Q   A   E   D   L   A   V   Y   Y   C   Q   N   D

301  CAT ATT TAT CCG TAC ACG TTC GGA GGG GGG ACC AAG CTG GAA ATA AAA  348
     H   I   Y   P   Y   T   F   G   G   G   T   K   L   E   I   K
```

FIG.3B

SEQUENCE LISTING

<160> NUMBER OF SEQ ID NOS: 8

<210> SEQ ID NO 1
<211> LENGTH: 37
<212> TYPE: DNA
<213> ORGANISM: Homo sapiens

<400> SEQUENCE: 1
cccgtctaga ggagayatyg twatgaccca gtctcca                                37

<210> SEQ ID NO 2
<211> LENGTH: 22
<212> TYPE: DNA
<213> ORGANISM: Homo sapiens

<400> SEQUENCE: 2
gtttkatctc gagcttkgts cc                                                22

<210> SEQ ID NO 3
<211> LENGTH: 17
<212> TYPE: DNA
<213> ORGANISM: Homo sapiens

<400> SEQUENCE: 3
aggtsmarct kctcgag                                                      17

<210> SEQ ID NO 4
<211> LENGTH: 34
<212> TYPE: DNA
<213> ORGANISM: Homo sapiens

<400> SEQUENCE: 4
tgmrgagacg gtgaccgtrg tyccttggcc ccag                             34

<210> SEQ ID NO 5
<211> LENGTH: 408
<212> TYPE: DNA
<213> ORGANISM: Homo sapiens
<220> FEATURE:
<221> NAME/KEY: CDS
<222> LOCATION: (1)..(408)
<223> OTHER INFORMATION:

<400> SEQUENCE: 5

```
atg aga gtg ctg att ctt ttg tgg ctg ttc aca gcc ttt cct ggt atc      48
Met Arg Val Leu Ile Leu Leu Trp Leu Phe Thr Ala Phe Pro Gly Ile
 1               5                  10                  15 ctg tct gat gtg cag ctt cag gag tcg gga cct ggc ctg gtg aag cct      96
Leu Ser Asp Val Gln Leu Gln Glu Ser Gly Pro Gly Leu Val Lys Pro
             20                  25                  30 tcc cag tct ctg tcc ctc acc tgc tct gtc act ggt tac tca atc acc     144
Ser Gln Ser Leu Ser Leu Thr Cys Ser Val Thr Gly Tyr Ser Ile Thr
         35                  40                  45 agt ggt tat gcc tgg aac tgg atc cgg cag ttt cca gga aac aaa ctg     192
Ser Gly Tyr Ala Trp Asn Trp Ile Arg Gln Phe Pro Gly Asn Lys Leu
     50                  55                  60 gag tgg atg ggc tac ata agc tac agt ggt ttc act agc tac aac cca     240
Glu Trp Met Gly Tyr Ile Ser Tyr Ser Gly Phe Thr Ser Tyr Asn Pro
 65                  70                  75                  80 tct ctc aga agt cga atc tct ttc act cga gac aca tcc aag aac cag     288
Ser Leu Arg Ser Arg Ile Ser Phe Thr Arg Asp Thr Ser Lys Asn Gln
                 85                  90                  95 ttc ttc ctg cag ttg aat tct gtg act tct gag gac aca gcc aca tat     336
Phe Phe Leu Gln Leu Asn Ser Val Thr Ser Glu Asp Thr Ala Thr Tyr
            100                 105                 110 tac tgt gca aga tgg gac tac ggt act acc tac ggg tac ttc gat gtc     384
Tyr Cys Ala Arg Trp Asp Tyr Gly Thr Thr Tyr Gly Tyr Phe Asp Val
        115                 120                 125 tgg ggc caa ggg act acg gtc acc                                     408
Trp Gly Gln Gly Thr Thr Val Thr
    130                 135
```

<210> SEQ ID NO 6
<211> LENGTH: 136
<212> TYPE: PRT
<213> ORGANISM: Homo sapiens

<400> SEQUENCE: 6

Met Arg Val Leu Ile Leu Leu Trp Leu Phe Thr Ala Phe Pro Gly Ile
 1               5                  10                  15

Leu Ser Asp Val Gln Leu Gln Glu Ser Gly Pro Gly Leu Val Lys Pro
             20                  25                  30

Ser Gln Ser Leu Ser Leu Thr Cys Ser Val Thr Gly Tyr Ser Ile Thr
         35                  40                  45

Ser Gly Tyr Ala Trp Asn Trp Ile Arg Gln Phe Pro Gly Asn Lys Leu
     50                  55                  60

```
Glu Trp Met Gly Tyr Ile Ser Tyr Ser Gly Phe Thr Ser Tyr Asn Pro
 65                  70                  75                  80

Ser Leu Arg Ser Arg Ile Ser Phe Thr Arg Asp Thr Ser Lys Asn Gln
                 85                  90                  95

Phe Phe Leu Gln Leu Asn Ser Val Thr Ser Glu Asp Thr Ala Thr Tyr
            100                 105                 110

Tyr Cys Ala Arg Trp Asp Tyr Gly Thr Thr Tyr Gly Tyr Phe Asp Val
            115                 120                 125

Trp Gly Gln Gly Thr Thr Val Thr
            130             135

<210> SEQ ID NO 7
<211> LENGTH: 348
<212> TYPE: DNA
<213> ORGANISM: Homo sapiens
<220> FEATURE:
<221> NAME/KEY: CDS
<222> LOCATION: (1)..(348)
<223> OTHER INFORMATION:

<400> SEQUENCE: 7 tct aga gga gat atc gtt atg acc cag tct cca tcc tcc ctg agt gtg    48
Ser Arg Gly Asp Ile Val Met Thr Gln Ser Pro Ser Ser Leu Ser Val
 1               5                  10                  15 tca gca gga gag aag gtc act atg agc tgc aag tcc agt cag agt ctg    96
Ser Ala Gly Glu Lys Val Thr Met Ser Cys Lys Ser Ser Gln Ser Leu
            20                  25                  30 tta aac agt aga aat caa aag aac tac ttg gcc tgg tac cag cag aaa   144
Leu Asn Ser Arg Asn Gln Lys Asn Tyr Leu Ala Trp Tyr Gln Gln Lys
        35                  40                  45 cca gga cag cct cct aaa ctt ttg atc tac ggg gta ttt att agg gat   192
Pro Gly Gln Pro Pro Lys Leu Leu Ile Tyr Gly Val Phe Ile Arg Asp
 50                  55                  60 tct ggg gtc cct gat cgc ttc aca ggc agt gga tct gga acc gat ttc   240
Ser Gly Val Pro Asp Arg Phe Thr Gly Ser Gly Ser Gly Thr Asp Phe
 65                  70                  75                  80 act ctt acc atc agc agt gtg cag gct gaa gac ctg gca gtt tat tac   288
Thr Leu Thr Ile Ser Ser Val Gln Ala Glu Asp Leu Ala Val Tyr Tyr
                 85                  90                  95 tgt cag aat gat cat att tat ccg tac acg ttc gga ggg ggg acc aag   336
Cys Gln Asn Asp His Ile Tyr Pro Tyr Thr Phe Gly Gly Gly Thr Lys
            100                 105                 110 ctg gaa ata aaa                                                    348
Leu Glu Ile Lys
            115

<210> SEQ ID NO 8
<211> LENGTH: 116
<212> TYPE: PRT
<213> ORGANISM: Homo sapiens

<400> SEQUENCE: 8

Ser Arg Gly Asp Ile Val Met Thr Gln Ser Pro Ser Ser Leu Ser Val
 1               5                  10                  15

Ser Ala Gly Glu Lys Val Thr Met Ser Cys Lys Ser Ser Gln Ser Leu
            20                  25                  30

Leu Asn Ser Arg Asn Gln Lys Asn Tyr Leu Ala Trp Tyr Gln Gln Lys
        35                  40                  45

Pro Gly Gln Pro Pro Lys Leu Leu Ile Tyr Gly Val Phe Ile Arg Asp
 50                  55                  60
```

-continued

```
Ser Gly Val Pro Asp Arg Phe Thr Gly Ser Gly Ser Gly Thr Asp Phe
65                  70                  75                  80

Thr Leu Thr Ile Ser Ser Val Gln Ala Glu Asp Leu Ala Val Tyr Tyr
                85                  90                  95

Cys Gln Asn Asp His Ile Tyr Pro Tyr Thr Phe Gly Gly Gly Thr Lys
            100                 105                 110

Leu Glu Ile Lys
        115
```

DETECTION OF SMALL MOLECULES BY USE OF A PIEZOELECTRIC SENSOR

The present application is the national stage under 35 U.S.C. 371 of international application PCT/IL00/00048, filed Jan. 25, 2000 which designated the United States, and which international application was published under PCT Article 21(2) in the English language.

FIELD OF THE INVENTION

The present invention is generally in the field of sensors, and concerns a sensing apparatus, system and method for use in detecting of small molecules in a sample.

PRIOR ART

In the following description, reference will be made to several prior art documents shown in the lists below. These references will be referred to in the text by indicating the number from this list.

REFERENCES

1. Shons, A, Dorman, F., Najarian, J., *J. Biomed. Mater. Res.,* 6:565 (1972).
2. Suleiman, A. A., and Guilbault, G. G., *Analyst,* 119:2279, (1994).
3. Ward, M. D., and Buttry, D. A., *Science,* 249:1000, (1990).
4. Oliveria, J. R., and Silver, S. F., U.S. Pat. No. 4,242,096, (1980).
5. Rice, T. K., U.S. Pat. No. 4,236,893, (1980).
6. Rice, T. K., U.S. Pat. No. 4,314,821, (1982).
7. Roederer, J. E., Bastiaans, G. J., *Anal. Chem.,* 55:2333, (1983).
8. Roederer, J. E., Bastiaans, G. J., U.S. Pat. No. 4,735,906, (1988).
9. Muramatsu, H., Dicks, J. M., Tamiya, E., and Karube, I., *Anal. Chem.,* 59:2760, (1987).
10. Mueller-Schulte, D., and Laurs, H., CA. 112(7), 51807 g, (1990).
11. Muramatsu, H., Kajiwara, K., Tamiya, E., and Karube, I., *Anal. Chim. Acta,* 188:257, (1986).
12. Muramatsu, H., Watanabe, Y., Hikuma, M., Ataka, T., Kubo, I., Tamiya, E. and Karube, I., *Anal, Lett.,* 22:2155, (1989).
13. Konig, B., Grätzel, *Anal. Lett.,* 26:1567, (1993).
14. PCT published application WO 97/04314.

BACKGROUND OF THE INVENTION

The linear relationship between the change in the oscillation frequency of a piezoelectric crystal and the mass variation on the crystal as a result of binding or absorption phenomena, has been used to advantage in a gravimetric monitoring of antigen-antibody binding. The mathematical relationship between the frequency changes of a piezoelectric crystal, $\Delta f$, and mass changes, $\Delta m$, on the crystal is given by the following Sauerbrey equation:

$$\Delta f = -2.3 \times 10^6 f_o^2 \cdot \Delta m / A$$

where $f_o$ is the fundamental resonance frequency of the crystal prior to the mass variation and A is the surface area of deposited mass. For example, for a crystal exhibiting a fundamental frequency of 9 MHz and surface area of 1 cm$^2$, a mass-change on the crystal that corresponds to $1 \times 10^{-9}$ g, will stimulate a frequency change, $\Delta f$, of 6 Hz.

The first analytical use of piezoelectric crystals in relation to antigen-antibody (Ag-Ab) interactions was reported in 1972[1], where a nyebar precoated crystal was further coated via hydrophobic interactions, with bovine serum albumin (BSA) and the association of the BSA-Ab to the crystal was monitored by the frequency changes. Since then, the piezoelectric detection of antigens and antibodies by piezoelectric means or the quartz crystal microbalance (QCM) has been adopted in a series of analytical studies. The progress in this area has been reviewed by Suleiman et al., 1994[2] and Ward et al., 1990[3].

Several patents describe the application of QCM for the analysis of antigens and antibodies. Physical adsorption of antigens to a crystal was used as a means for the detection of antigens by interacting the crystal with a mixture of the analyte antigen and a predetermined amount of Ab[4]. The decrease in the antigen concentration was inversely related to the antigen concentration in the sample. In two patents by Rice[5,6], methods for the determination of Abs by QCM were disclosed. The antigen was immobilized on a polymer precoated crystal and the frequency changes as a result of Ab association related to the analyte Ab concentration in the sample. By this method, human IgG against honey bee venom, phospholipase A, and keyhold limpet hemocyanine were analyzed[7]. However, non-specific binding to the crystal interfered with the analyses. In a follow-up patent[8], the detection of low molecular weight components by a pre-coated crystal with the anti-Ab and competitive binding assay of the Ab-low molecular weight analyte was described. All of these analyses were performed by treatment of the crystals in solution and subsequent frequency measurements in air. This two-step solution/gas procedure allows improvement of the sensitivity of the resonating QCM, but introduces technical complications and the interference of hydration/dehydration phenomena that are reflected in the frequency parameters.

Piezoelectric immunoassaying in the liquid phase has important technical advantages as it allows stationary and flow analysis of aqueous samples. The method suffers, however, from a basic physical limitation due to substantially lower frequency changes of the crystal as a result of the solution viscosity. QCM immunoassays in solution were reported by Roederer[7] and addressed in a follow-up patent[8]. The quartz crystal was modified with glycidoxypropyltrimethoxy silane (GOPS), and the surface-modified crystal was then further modified by anti-human IgG antibody and then applied for the piezoelectric detection of human IgG. The detection limit of the device was determined to be 13 μg·ml$^{-1}$. A closely related approach was adopted by Muramatsu et al.[9] where the quartz crystals were surface-modified by γ-aminopropyl triethoxy silane and further derivatized by protein A. The surface-modified crystals were then applied for the determination of human IgG in the concentration range 10$^{-6}$–10$^{-2}$ mg·ml$^{-1}$. A related patent disclosed the piezoelectric analysis of thyroxine using a polyamide 6 polymer coating and anti-thyroxine Ab as sensing interface[10].

Piezoelectric analysis of high molecular weight antigens such as microbial cells was addressed using antibody-coated quartz-crystals. *C. albicans* cells in the concentration range $1 \times 10^6$–$5 \times 10^8$ cells·ml$^{-1}$ were analyzed by an anti-*Candida albicans* Ab surface[11], *E. coli* with an anti-*E. coli* interface[12] and protein A-coated crystals acted as piezoelectric sensing interface for various bacteria including *Salmonella, Shigella, Yersinia* and *E. coli*[13]. Various schemes allowing efficient use of QCM in assaying analytes in a liquid media have been described in WO 97/04314[(14)].

QCM techniques were used hitherto only for detection of interaction with substances of relatively high molecular weight, e.g. proteins and other macromolecules. The QCM techniques are generally considered not sufficiently sensitive for detection of substances of a low molecular weight.

GENERAL DESCRIPTION OF THE INVENTION

The present invention has as its object the provision of an apparatus, system and method for detecting small assayed molecules in a sample.

The term "detection" as used herein means to denote either or both of a qualitative determination of the existence of an explosive in a sample or a quantitative analysis of the amount or concentration of such an explosive in the sample.

The term "sample" means to denote a liquid preparation which may either be a specimen in which an explosive is to be detected, may be a fractionation product which contains the explosive if present in a sample, or in general any preparation in which the level of explosive is indicative to the level of explosive in the specimen. The specimens which may be tested in accordance with the invention may be an original liquid specimen, e.g. samples withdrawn from water reservoirs, may be a soil specimens or gas specimens. In the case of gasses or soil specimens, these are typically first reacted with the liquid in a manner that at least some of the explosive molecules if present in the specimen will be dissolved in the liquid, typically an aqueous solution.

The term "small molecule" as used herein means to denote a molecule having a molecular weight such that its binding to a sensing surface at an amount expected to be found in a sample will not give rise to a detectable mass change of the sensing surface. In particular, the term "small molecules" as used herein applies to molecules having a molecular weight below about 5,000 Dalton, typically below about 1,500 Dalton, at times even below about 500 Dalton. Specific examples of small molecules may be detected in accordance with the invention are explosive molecules including, but not limited to, DNT and TNT.

Explosives have a relatively low volatility and accordingly, a specimen even if taken from the vicinity of an explosive, typically contains only a small amount of such molecules. Thus, any method intended for sensing the presence of explosive molecules in a sample should be highly sensitive and adapted for detecting a small amount of explosive molecules. This may be the case also with respect to other types of low molecular weight molecules which may be assayed, such as drugs, e.g. heroin, cocaine, etc.

The present invention provides, by a first of its aspects, an apparatus for detecting small assayed molecules in a sample, comprising:

(a) a sensing member comprising a piezoelectric crystal having at least one sensing surface which can interact with a medium in contact therewith a by either binding a first indicator agent from the medium, or by releasing a second indicator agent originally immobilized on the sensing surface into the medium; the medium being either the sample in which case the assayed molecule present, causes the release of the second indicator agent from the at least one sensing surface, or being a treated sample preparation obtained by reacting the sample with one or both of a reagent solution or sample-processing hardware, such that said medium comprises a first indicator agent or a second indicator agent-releasing species at a concentration of said agent or species which is in correlation to the concentration of the assayed molecule in the sample, the binding or release resulting in a change of mass of the sensing surface;

(b) a testing cell for holding said medium and bringing it into contact with said at least one sensing surface; and (c) an electric or electronic utility for inducing vibrations in the piezoelectric crystal and measuring resonance frequency thereof, a change in resonance frequency after contact between the sensing surface and the medium, indicating presence of the explosive in the sample.

The invention also provides a method for detecting a small molecule in a sample, comprising:

(a) providing a sensing member comprising a piezoelectric crystal having at least one sensing surface which can interact with a medium in contact therewith by either binding a first indicator agent from the medium, or by releasing a second indicator agent originally immobilized on the sensing surface into the medium;

(b) contacting the at least one sensing surface with a medium being either the sample in which case the assayed molecule if present causes the release of the second indicator agent from the sensing surface, or being a treated sample preparation obtained by reacting the sample with one or both of a reagent solution or sample-processing hardware, such that said medium comprises a first indicator agent or a second indicator agent-releasing species, at a concentration of said agent or species which is in correlation to the concentration of the assayed molecule in the sample, the binding or release resulting in a change of mass of the sensing surface;

(c) inducing vibrations in the piezoelectric crystal and measuring resonance frequency thereof; and (d) determining whether a change in resonance frequency after contact between the sensing surface and the medium occurred, such change indicating presence of the assayed molecule in the sample.

In accordance with a preferred embodiment of the invention the small molecule is an explosive. Particular, non-limiting examples of explosives are dinitrotoluene (DNT) and 2,4,6-trinitrotoluene (TNT).

The apparatus of the invention may be designed to provide an all-or-none response, namely an indication whether the assayed small molecule is present in the sample. Alternatively, the apparatus may also be used and designed to provide a quantitative response, namely a response that depends on the level of the assayed molecule in the sample.

In accordance with one embodiment of the invention, said at least one sensing surface carries capturing agents which bind to neutralizing agents at an assayed molecule-binding domain thereof. In accordance with this embodiment, the sensing member is contacted with a medium which contains capturing agents at a concentration which inversely reflects the concentration of the assayed molecules in the sample. In accordance with this embodiment, the sample is first contacted with a reagent solution comprising the neutralizing agents which then bind the assayed molecules if such are in the sample. This treated preparation is then brought into contact with the at least one sensing surface. The neutralizing agents, bound to the assayed molecules, are not any more free to bind to the capturing agents. Thus, where the sample is free from the assayed molecules, a relatively large number of neutralizing agents will be free to bind to the capturing agents on the at least one sensing surface. Where the sample contained the assayed molecules, there will be less neutralizing agents free to bind to the capturing agents. Thus, a decrease in the resonance frequency, indicative of increased immobilized mass on a surface, is a reverse indication of the presence of the assayed molecule in the sample: a relatively large decrease in resonance frequency indicates absence or little concentration of the assayed molecules in the sample, and no or only a little decrease indicates existence of the assayed molecule in the sample. The extent of decrease in resonance frequency versus control can be used as inverse indication of the concentration of the assayed molecule in the sample. The capturing agents are typically residues or moieties of the assayed molecules and the neutralizing agents may comprise first antibodies which have a relatively high specific binding affinity to the assayed molecules.

The term "antibody" as used herein is meant to encompass antibodies of various kinds including, but not limited to IgG or IgM antibodies which may be polyclonal or monoclonal (mAb). In addition, the term "antibody" encompasses also various derivatives of antibodies which include the antigen-binding domain of the antibody. Such derivatives may include Fc-less antibodies (antibodies devoid of the constant region), single chain antibodies, constructs comprising only the variable region of the antibodies, etc.

In accordance with another embodiment of the invention, the at least one sensing surface carries residues or moieties of the assayed molecules bound to first antibodies, which competitively bind to soluble assayed molecules in a medium which comes into contact with the at least one sensing surface. In the presence of the assayed molecule in said medium the antibodies are released from the at least one sensing surface to bind the assayed molecules. An assay where an apparatus in accordance with this embodiment is used, involves an essential competition reaction between the assayed molecule and the capturing agent on binding to the neutralizing agent. In accordance with this embodiment the sample is brought into direct contact with the at least one sensing surface. In the presence of the assayed molecule in the sample, neutralizing agents are released from the sensing surface to find to the assayed molecules in this surrounding solution. Thus, an increase in the resonance frequency, indicative of a reduction in mass immobilized on the at least one sensing surface, only indicate the presence of the assayed molecule in the sample. Against this, lack of change or little change in the resonance frequency indicates no or only a small amount of the assayed molecule in the sample.

The first antibodies in both of the above embodiments may be bound or complexed with a mass-increasing agent for the purpose of amplifying the response. A mass-increasing agent may, for example, be a large molecular complex, e.g. a protein, conjugated to the antibody, or a colloid particle, e.g. a gold colloid, bound to the first antibody. Such a second antibody may be conjugated to or complexed with other agents such as to a colloid particle, to a molecular complex, etc. In addition, the mass-increasing agent may, by one preferred embodiment, comprise a second antibody which binds to said first antibody. In addition, by another preferred embodiment, the mass-increasing agent, which may be any of the agents mentioned above, comprises avidin or streptavidin which then binds to a biotin residue conjugated to the first antibody. The mass-increasing agent may be added either prior to allowing the first antibodies to bind to the at least one sensing surface or thereafter. Where a mass-increasing agent is used, the change of mass as a result of binding to release of the neutralizing agent will be considerably larger, and consequently there will be a larger signal-to-noise ratio.

As stated above, the assayed molecule is typically an explosive molecule such as DNT or TNT. In such a case said first antibodies, which are typically mAbs, are preferably mAbs with the binding characteristics of 5B3, particularly in the 5B3 mAb itself.

The present invention further provides a system for detecting small assayed molecules in a sample which comprises the above apparatus as well as one or both of reagents and hardware for processing the sample or for introducing it into the assayed cell of the apparatus. The system typically has hardware components for propelling the sample into the assayed cell. The system may have various additional hardware and reagents which are intended for processing of the sample, for contacting the sample with reagents, etc.

In accordance with one embodiment, to be referred to herein as the "displacement embodiment" the system comprises:
(a) a sensing member comprising a piezoelectric crystal having at least one sensing surface which carries residues or moieties of said assayed molecules bound to neutralizing agents, e.g. anti-assayed molecule antibodies;
(b) a testing cell for holding a medium and bringing it into contact with said at least one sensing surface, whereby in the present of the assayed molecules in the medium, at least some of said antibodies are released into the medium;
(c) hardware for introducing the sample into the testing vessel; and
(d) an electric or electronic utility for inducing vibrations in the piezoelectric crystal and measuring resonance frequency thereof, a reduction in resonance frequency after contact between the sensing surface and the medium, indicating presence of said assayed molecule in the sample.

In accordance with the displacement embodiment the sample is contacted with the sensing surface and then vibrations are induced in the piezoelectric crystal to measure resonance frequency. Owing to binding competition, where the sample comprises assayed molecules, some of the neutralizing agents are released and bind to the assayed molecules in the sample which results in reduction of mass of the sensing surface and thus an increase in the resonance frequency. Such an increase is then indicative that the assayed molecule is present in the sample.

In accordance with another embodiment, to be referred to herein as the "competition embodiment", the system comprises:
(a) a sensing member comprising a piezoelectric crystal having at least one sensing surface which carries residues or moieties of the assayed molecules;
(b) a reagent system comprising neutralizing agents, e.g. anti-assayed molecule antibodies;
(c) a testing cell for holding a medium and bringing it into contact with said at least one sensing surface, whereby in the presence of the assayed molecules in the medium, at least some of said antibodies are released into the medium;
(d) an arrangement for contacting the sample with said reagent system to obtain a treated sample preparation and for introducing the treated sample preparation into the testing vessel; and
(e) an electric or electronic utility for inducing vibrations in the piezoelectric crystal and measuring resonance frequency thereof, a decrease in resonance frequency after contact between the sensing surface and the treated sample preparation, indicating that the sample is free of the assayed molecules.

In accordance with the competition embodiment the sample is contacted with neutralizing agents and incubated for a time allowing the neutralizing agents to bind the assayed molecules if such are present in the sample. This treated sample preparation is then contacted with the at least one sensing surface. In the presence of the assayed molecules in the sample, the neutralizing agents will bind these molecules and will thus not be free to bind to the capturing agents. Thus, in the presence of the assayed molecules in the sample, there will be no or little change in the resonance frequency of the crystal. If the sample is free of the assayed molecule, the neutralizing agents will be free to bind to the capturing agents which will give rise to a significant mass increase and hence to a decrease in the crystal's resonance frequency. Thus, such a decrease will indicate absence of the assayed molecules from the sample.

In accordance with another embodiment, to be referred to herein as the "basic filtration embodiment", the system comprises:
(a) a sensing member comprising a piezoelectric crystal having at least one sensing surface which carries capturing agents for binding to neutralizing agents;
(b) a testing cell for holding a medium and bringing it into contact with said at least one sensing surface;
(c) a reagent system comprising the neutralizing agents which can bind to the assayed molecules;
(d) an arrangement for contacting the sample with the reagent system under condition and for a time permitting binding of the neutralizing agent to the assayed molecules, to obtain a treated sample preparation;
(e) a filtration system for filtering out from said treated sample preparation neutralizing agents unbound to an explosive molecule to obtain a filtrate essentially devoid of such unbound neutralizing agents;
(f) arrangement for transfer of said filtrate to said testing cell; and
(g) an electric or electronic utility for inducing vibrations in the piezoelectric crystal and measuring resonance frequency thereof, an increase in resonance frequency after contact between the sensing surface and the filtrate, indicating presence of the assayed molecules in the sample.

In accordance with the basic filtration embodiment, the sample is contacted with a neutralizing agent, typically an antibody, which can bind to the assayed molecules. The incubation of the sample with the neutralizing agent is contacted under conditions and for a time permitting binding of the neutralizing agents to the assayed molecules thus obtaining a treated sample preparation. The treated sample preparation is then filtered through the filtration system to filter out neutralizing agents which are unbound to the assayed molecules so as to obtain a filtrate essentially devoid of such unbound neutralizing agents. The filtrate is then contacted with the at least one sensing surface. Where the sample contained the assayed molecules, the neutralizing agents will filter through the filtration system and will eventually bind to the at least one sensing surface resulting in a mass increase. In the absence of the assayed molecules from the sample, the neutralizing agents will be captured within the filtration system and contact of the filtrate with the sensing surface will not give rise to an increase in mass. Thus, a decrease in resonance frequency, indicative of binding of neutralizing agents to the at least one sensing surface, will signify presence of the assayed molecules in the sample.

In accordance with yet another embodiment of the invention, to be referred to herein as the "enzyme embodiment", the system comprises:

(a) a sensing member comprising a piezoelectric crystal having at least one sensing surface which carries capturing agents for binding to neutralizing agents;
(b) a testing cell for holding a medium and bringing it into contact with said at least one sensing surface;
(c) a reagent system comprising neutralizing agents which can bind to the assayed molecules, said neutralizing agent being conjugated to an enzyme which can catalyze a reaction yielding an insoluble reaction product;
(d) an arrangement for contacting the sample with the reagent system under condition and for a time permitting binding of the neutralizing agent to the assayed molecules, to obtain a treated sample preparation;
(e) a filtration system for filtering out from said treated sample preparation neutralizing agents unbound to an assayed molecule to obtain a filtrate essentially devoid of such unbound neutralizing agents;
(f) arrangement for transfer of said filtrate to said testing cell;
(g) an ensemble of reagents and conditions for inducing said enzyme to catalyze the reaction yielding the insoluble reaction product; and
(h) an electric or electronic utility for inducing vibrations in the piezoelectric crystal and measuring resonance frequency thereof, an increase in resonance frequency after contact between the sensing surface and the filtrate or after permitting the enzyme to catalyze said reaction, indicating presence of the assayed molecule in the sample.

This embodiment is somewhat similar to that previously described, the difference is that there is an additional amplification sequence in which the enzyme is permitted to catalyze a reaction giving rise to unsoluble reaction products which in the presence of the assayed molecule in the sample, give a higher increase in mass and hence a higher decrease in resonance frequency.

The invention also provides, by another of its aspects, a monoclonal antibody designated herein as 5B3. The nucleotide sequence and the deduced amino acid sequence of the heavy and light change variable regions of the 5B3 monoclonal antibody are depicted in FIGS. 3A and 3B, respectively. An antigen-binding portion of an antibody can be fused (chemically or by creating a fused gene containing the coding sequence and expressing such a sequence) in a manner such that said antigen-binding portion in the resulting fused protein retains its antigen-binding specificity. Thus, the present invention encompasses in its scope any protein, particularly an antibody, which includes an antigen-binding portion with substantially the same antigen-binding specificity of the 5B3 antibody and having two cooperating peptide sequences being the sequences of FIG. 3A and FIG. 3B, or of altered sequence thereof, as defined below. Such an antibody may be of any known type, e.g. IgM or IgG, may be a fragment of an antibody comprising the antigen-binding domain, e.g. Fab, an antibody without the Fc region, a single chain antibody, etc.

As will readily be appreciated by the artisan it is possible, at times, to alter the variable antigen-binding portion, to obtain an altered portion, by adding one or more amino acid residues, deleting one or more amino acid residues or replacing one or more amino acid residues by other residues, such that the altered portion retains substantially the same antigen-binding specificity of the non-altered portion, i.e. that of the 5B3 antibody. Thus, such altered variable regions as well as antibodies or other constructs including such altered variable regions, with the altered variable region retaining substantially the same antigen-binding specificity of the non-altered variable region (namely that depicted in FIGS. 3A and 3B) are also included within the scope of the present invention.

The term "retaining substantially the same antigen-binding specificity" should be understood as meaning that the altered portion has the ability to bind an antigen (e.g. TNT or DNT) bound by the non-altered portion with an affinity which is considerably higher (typically by several orders or magnitude) than the affinity of binding to other antigens. Such altered portion may have a binding affinity to the antigen which may be about the same as that of the non-altered portion or with the binding affinity which may at times be somewhat higher or somewhat lower than that of the non-altered portion.

The at least one sensing surface typically carries a metal plate made particularly of such metals having the capability to associate chemical with, attach or chemisorb a sulfur-containing moiety. The metal plates are preferably made of or coated by metals such as gold, platinum, silver or copper. Where the capturing agents are carried on metal plates these typically thus serve as a dual role of both serving as a carrying matrix for the capturing agent as well as being an electrode of the piezoelectric crystal device.

The capturing agents are typically immobilized to the metal plates by means of a sulfur containing moiety bound thereto, e.g. in the manner described in WO 97/04314[(14)].

The term "neutralizing agent" which is used herein means to denote an agent which has a specific binding affinity to the assayed molecules. In accordance with one embodiment the neutralizing agent is an antibody with a specific binding affinity to the assayed molecule. The embodiment in which the neutralizing agent is an antibody, typically a monoclonal antibody (mAb) is a preferred embodiment of the invention. However, the term "neutralizing agent" encompasses also other types of agents including, for example: a soluble receptor moiety containing the analyte binding domain, in which case the assayed molecule is said analyte; a soluble receptor moiety containing the binding domain of the enzymes' substrate wherein the assayed molecule is said substrate; and others. In addition, the neutralizing agent may also be a synthetic macromolecule which comprises one domain with binding affinity to the assayed molecule, e.g. a binding domain derived from an anti-assayed molecule antibody, conjugated or fused to a macromolecular moiety, e.g. a large polypeptide or protein. (Conjugation or fusion may be achieved, as known, by chemical binding, by genetic engineering techniques, etc.).

The invention will now be further illustrated in the following detailed description of some preferred embodiments, with reference made to the annexed drawings. As will be appreciated, this description is for the purpose of illustration only and is not intended to be limiting.

BRIEF DESCRIPTION OF THE DRAWINGS

FIG. 1A and FIG. 1B show the structure of the various haptens, being TNT derivatives (FIG. 1A) or DNT derivatives (FIG. 1B), which were used in the embodiments described herein. In the Figs. the abbreviation P denotes KLA, FγG or BSA, the abbreviation TNP-cap denotes TNP-caproic acid and the abbreviation 2,4-DNP-cap denotes 2,4-DNP-caproic acid.

FIG. 3A and FIG. 3B show, respectively, the nucleotide sequences (SEQ ID Nos. 5 and 7) and the deduced amino acid sequences (SEQ ID Nos. 6 and 8) of the 5B3 heavy and light chain variable regions.

DETAILED DESCRIPTION OF PREFERRED EMBODIMENTS

Figure 2A:
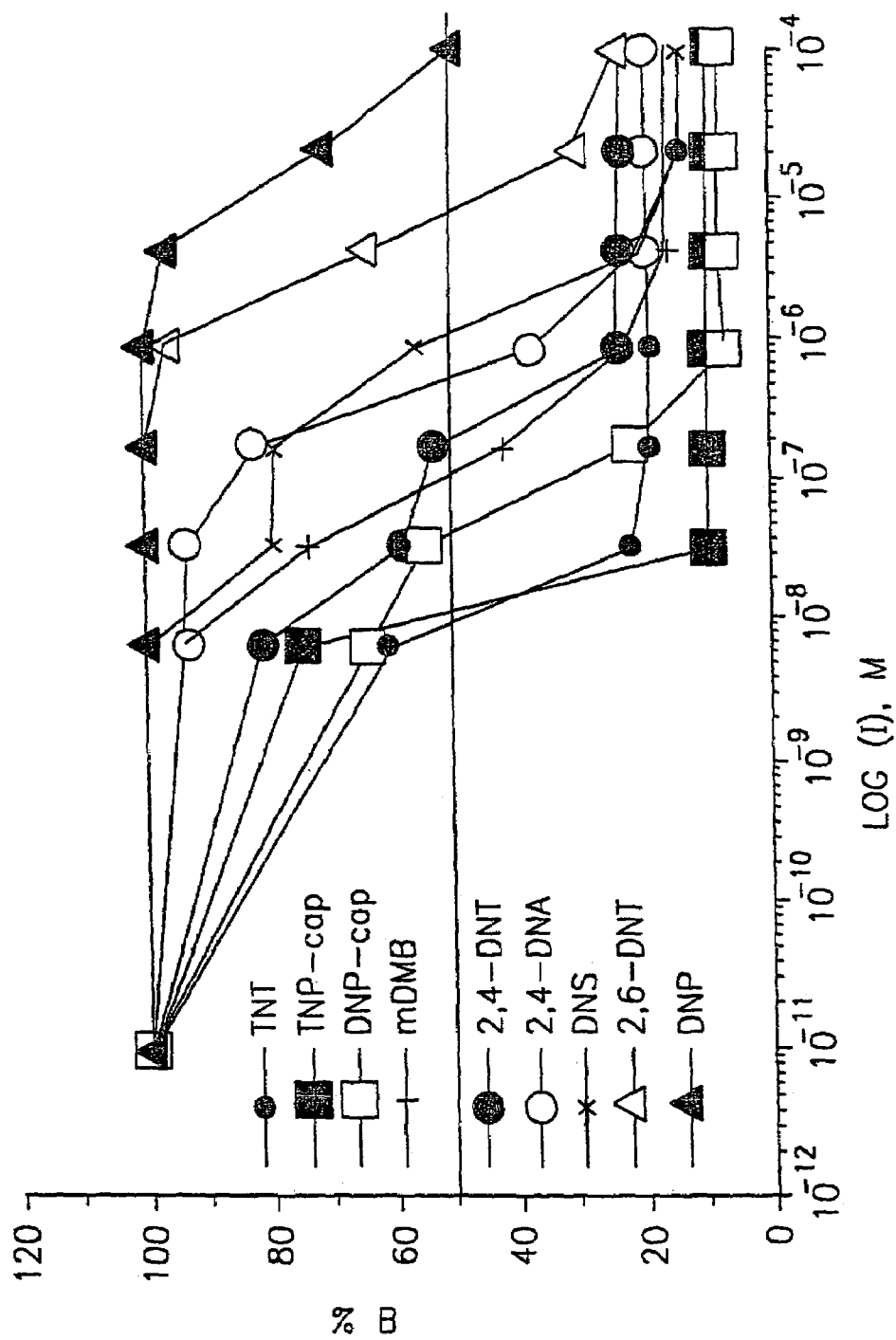
FIG. 2A shows inhibition profiles of binding (performed by ELISA, I denotes Inhibition and B denotes Binding) of 5B3 antibody to DNS-BSA (DNS coupled to BSA) in the presence of different inhibitors—TNT, TNP-caproic acid (TNP-cap), DNP-caproic acid (DNP-cap), mDNB, 2,4-DNA, DNS, 2,6-DNT and 2,4-DNP.

The following are some exemplary embodiments of the invention:

1. Anti-TNT Antibodies 1.1 Antigens/Immunogens

The following TNP-proteins have been used: $TNP_{40}$-KLH, $TNP_{33}$-BSA, $TNP_2$-FγG. To simulate the antigen subsequently used on the QCM crystal (see below), 2,4-dinitrosalicylic acid (DNS) coupled to BSA was used. Coupling between the TNT, DNT and derivatives and the protein was done using EDCI. The structure of TNT and derivatives as well as that of DNT and derivatives which were used is shown in FIGS. 1A and 1B.

As immunogen, 2,4,6-trinitrophenyl (TNP) was used which after coupling to a protein carrier looks very similar to TNT. TNP was coupled to a carrier protein (keyhold limpet hemocyanine (KLH) as immunogen or bovine serum albumin (BSA) and fowl gamma globulin (FγG) as antigen), by mixing 100 mg 2,4,6-trinitrobenze sulfonic acid (TNBS) with 100 mg protein at 02 M borate buffer pH 9.2 for 2 hours at 37° C. Following extensive dialysis against PBS, the TNP-proteins were filtered through a 45 μm filter and the molar ratio of TNP per protein was determined using molar extinction coefficient of 15,400 at 348 nm[1].

1.2 Immunization

Female BALB/c mice 8–10 weeks of age were immunized intradermally into the hind foot pads with 20 μg of TNP-KLH emulsified with Complete Freund's Adjuvant (CFA). Two weeks later, mice were injected subcutaneously with the same amount of antigen in CFA. A week following this boost, mice were bled and the anti-TNP antibody titre was determined in their sera using ELISA (see below). One month after the second boost, mice showing the highest antibody titre were boosted again intraperitoneally with 10 μg TNP-KLH in PBS on days −4 and −3 prior the cell fusion.

1.3 Preparation of 5B3 Monoclonal Antibody

Spleen cells of a mouse with the highest titre of binding antibodies (and specificity to TNT, see for detection details below) were fused with the NSO, murine myeloma cell line as described before (Eshhar, Monoclonal antibody strategy and techniques. In: *Hybridoma in Biotechnology and Medicine*, Springer, T., ed. Plenum Press, p. 1, 1985). Briefly, $10^8$ spleen cells were fused with $2 \times 10^7$ NSO myeloma cells using 41% PEG for 2 mins. at 37° C. Following removal of PEG by dilution and centrifugation, cells were resuspended in DMEM supplemented with 10% horse serum and HAT selective medium and distributed into 7 microculture plates. After 12 days incubation at 37° C. in 10% $CO_2$ saturated air, 50 μl aliquots of the hybridoma culture supernatants were removed in duplicate, one aliquot was assayed for binding to TNP-BSA, the second was assayed similarly, but following preincubation in the presence of TNT ($10^{-5}$ M). (See binding and inhibition assays (1.4 and 1.5 below). From 672 wells with hybridoma growth 32 scored positive for TNP-BSA binding. Six out of these were inhibited by $10^{-5}$ M TNT, out of which a hybridoma designated 5B3 was selected. The TNT-specific hybridomas were cloned and subcloned for 2–3 cycles and used to prepare ascites fluid which served as the source for purified antibodies.

For purification, the immunoglobulin fraction was precipitated from ascites fluids in 45% saturated ammonium sulfate, dialyzed against PBS and loaded on Protein-G-Agarose (Pharmacia) column. Monoclonal antibodies were eluted at pH 2.7, and dialyzed against PBS. Purified antibody preparations were stored in −70° C. The purified antibodies contained more than 96% active antibodies as verified by their ability to bind to antigen-columns.

1.4 Binding Assay for Anti-TNT Antibodies

Regular ELISA has been used to determine anti-TNT antibody activity. Microtitre plates (Maxisorb, NUNC) were coated with antigen (TNP-BSA, TNP-FγG, DNS-BSA) by incubating them with 100 μl of 2–10 μg/ml antigen in PBS for at least two hours in room temperature (RT). Following removal of antigen, plates were blocked by incubation for an hour at RT with PBS supplemented with 0.5% BSA and then washed with PBS supplemented with 0.05% Tween-20 (PBS-Tween). Supernatants or sera containing anti-TNP antibodies serially diluted in PBS supplemented with 0.01% PBS (100 µl) were then added to the washed plates and after 1 hour incubation at 37° C., antibodies were removed, plates were washed 3 times with PBS-Tween and 100 µl peroxidase-labeled anti-mouse Fab antibodies (Jackson Labs.), diluted according to the manufacturer's instructions were added. Plates were incubated for an hour at RT, washed (×3) and a peroxidase substrate (2,2'azinodi-(ethylbenzthiazoline sulfonic acid) diammonium salt (ATBS, Sigma) 1 mg/ml with 0.003% $H_2O_2$ in citrate-phosphate buffer, pH 4.5) was added. Reaction was stopped when sufficient color had been developed by the addition of 50 µl of 0.2 M citric acid and the OD at 620 nm was determined in ELISA plate reader.

1.5 Inhibition Assay

Figure 2B:
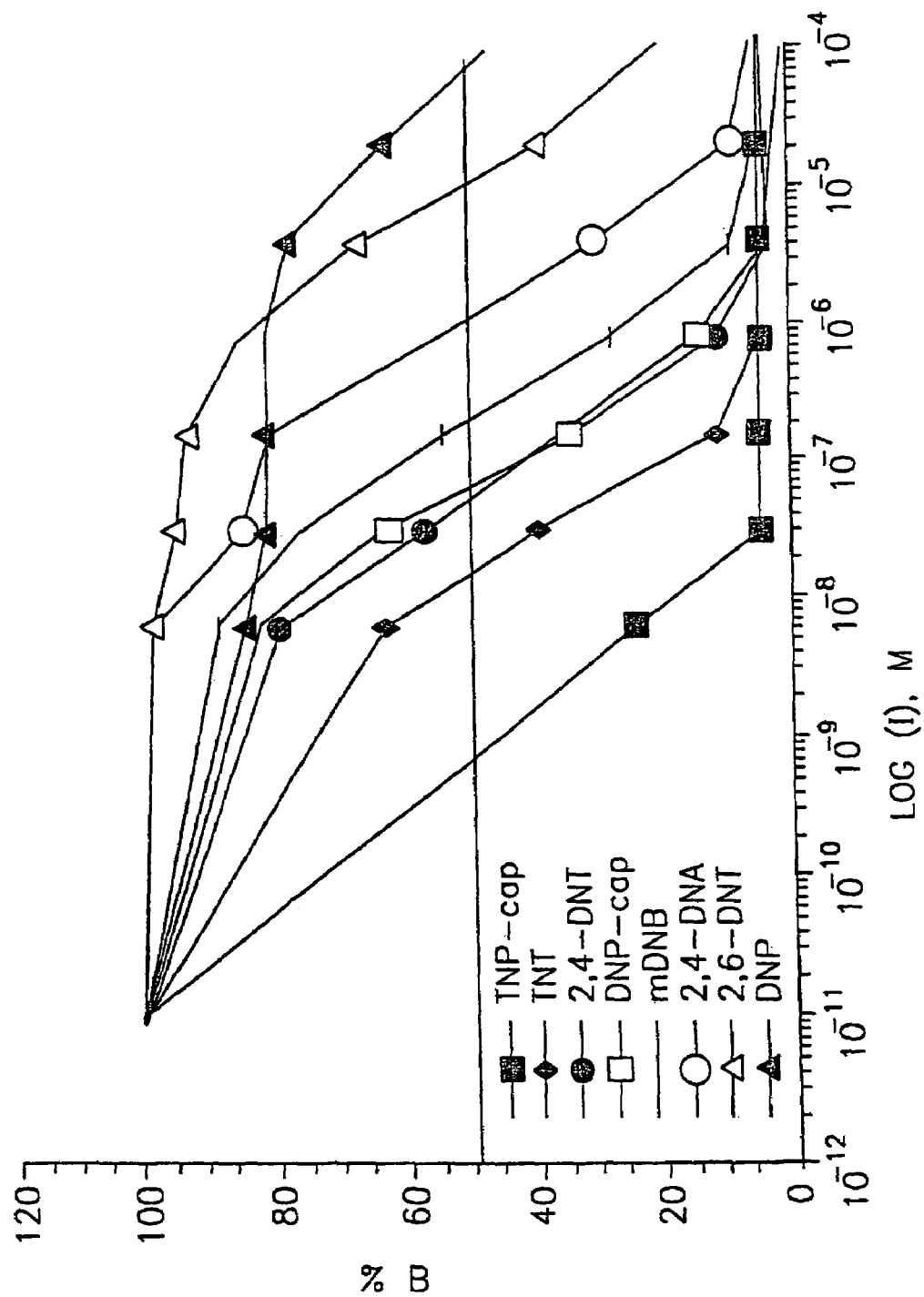
FIG. 2B shows inhibition profiles (performed by ELISA, I denotes Inhibition and B denotes Binding) of binding of 5B3 antibody to TNP$_2$-FγG (TNP coupled to FγG) in the presence of different inhibitors—TNT, TNP-caproic acid (TNP-cap), DNP-caproic acid (DNP-cap), mDNB, 2,4-DNA, DNS, 2,6-DNT and 2,4-DNP.

To determine the specificity and affinity of the antibodies (from immune sera, supernatants, ascites fluids or purified), antibody dilutions giving approx. 70% of the maximal binding were incubated with different concentrations of the hapten or hapten analogs for 30–60 mins. at RT. Mixtures of antibodies and the inhibitor (the hapten or the hapten analogs) were then transferred to ELISA plate coated with an antigen (DNS-BSA or $TNP_2$-FγG) and the residual binding capacity was determined. The results are shown in FIGS. 2A and 2B. Degree of inhibition was calculated from % binding of uninhibited sample minus background control. As a practical measure of affinity, the concentration of hapten which gave 50% inhibition, ($IC_{50}$), was determined.

1.6 Characteristics of 5B3 Antibody

5B3, is an IgG1 antibody, derived from a TNP-KLH immunized mouse. Some of its binding characteristics are summarized in the following Table 1, showing the $IC_{50}$ of various haptens of binding of the 5B3 antibody to TNP-antigen.

TNP-antigen. 5B3 mAb has two important additional features, which can also be seen in Table 1, which render it suitable for use in accordance with the invention: it does not bind avidly to 2,4-DNS which is used, by some embodiments, to coat the QCM crystal, and its binding to either TNP or DNS antigen can be blocked by very low amounts of TNT. These features were indeed found to be very useful since a concentration as low as 6 pgr of TNT could displace bound 5B3 from the QCM crystal and give a reproducible signal.

1.7 DNA and Protein Sequence of 5B3 Antibody cDNA was prepared from total RNA extracted from the 5B3 hybridoma using reverse transcriptase and oligo dT as 3' primer (Promega kit and protocol book for Reverse Transcription (RT)). To PCR amplify the cDNA coding for the variable region of the light chain, N5'VK2 as 5' and N3'VK as 3' oligonucleotide primers were used. For the amplification of the cDNA coding for the variable region of the heavy chain, N5'VH as 5' and N3'VH as 3' oligonucleotide primers were used. These oligonucleotide primers had the following sequences (SEQ ID Nos. 1 to 4, respectively):

N5'VK2  5'CCCGTCTAGAGGAGAYATYGTWATGACCCAGTCTCCA

NV'VK   5'GTTTKATCTCGAGCITKGTSCC

-continued

N5'VH   5'AGGTSMARCTKCTCGAG

N3'VH   5'TGMRGAGACGGTGACCG1TRGTYCCTTGGCCCCAG

In the above primer sequences the following letters have the following meanings:

| R = A or G | K = G or T |
| S = C or G | W = A or T |
| Y = C or T | M = A or C |

The first and the fourth of the above primers have already been described (Eshhur et al., *PNAS*, 90:720 (1993)).

PCR amplification was performed as previously described (The polymerase chain reaction, in: *Current Protocols in Molecular Biology*, Vol. 2, Chapter 15, John Wiley & Sons Inc., 1995).

Nucleotide sequencing was carried out directly from the PCR mixtures, reading both strands and using the primers described above. Automated sequencing using the Taq Dye Deoxy Terminator cycle sequencing kit and the ABI PRISM™ 377 DNA Sequencer was carried out. The nucleotide sequence and the deduced amino acid sequences of the 5B3 heavy and light chain variable regions are shown in FIG. 3A and FIG. 3B, respectively.

2. Preparation of a Layer of Capturing Agents on a QCM Crystal

In all the experiments reported herein, quartz crystals (AT-cut) sandwiched between two gold (Au) electrodes were used, which had a geometrical area of about $0.2$ $cm^2$, with a roughness factor which varied between 1.8 and 15. The crystal had a resonance frequency of around 9 MHz.

Figure 4:
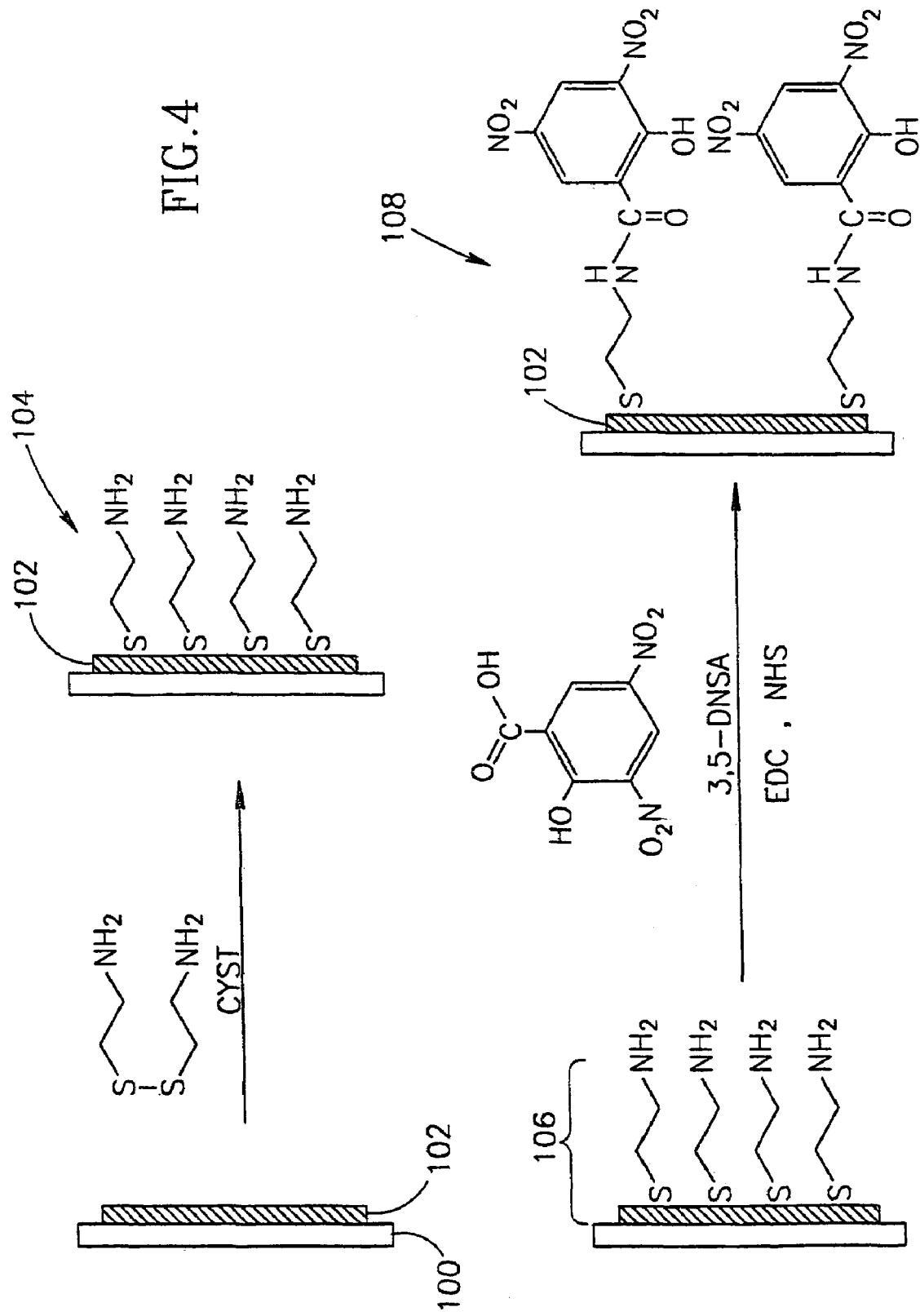
FIG. 4 shows a chemical scheme of production of a sensing surface containing a monolayer of capturing agents. The abbreviations EDC, NHS, CYST and 3,5-DNSA, denote, respectively, 1-ethyl-3-(3-dimethylaminopropyl) carbodiimide, N-hydroxysulfosuccinimde, cystamine and 3,5-dinitro-salicylic acid.
Figure 5:
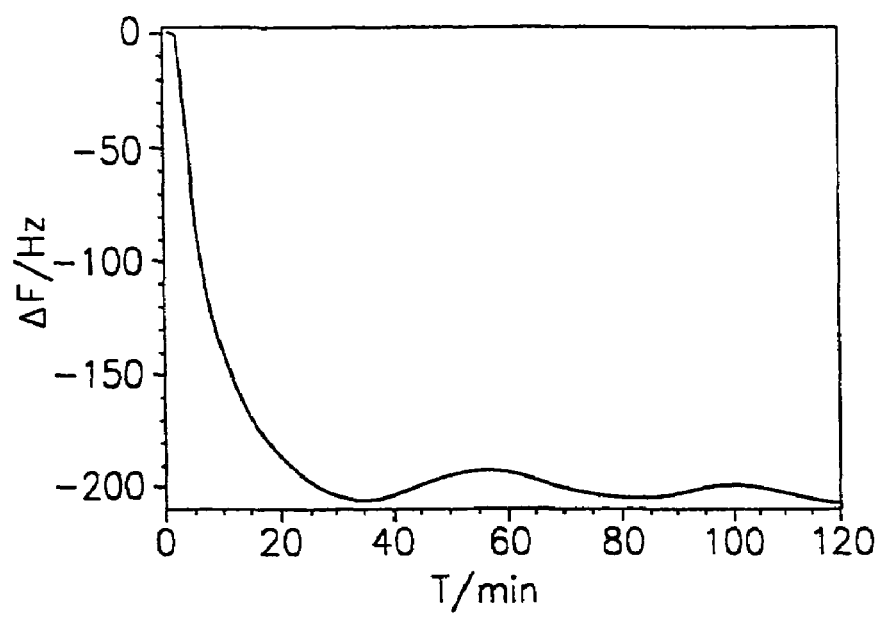
FIG. 5 shows the frequency changes (T/min denotes Time in minutes) of the crystal during its incubation with the cystamine and the formation of a system in a monolayer.

The chemical scheme of forming the electrodes can be seen in FIG. 4. The electrodes 102, carried on crystal 100 were cleaned by incubation in distilled water for 15 mins. which was following by rinsing three times with water and drying under a stream of nitrogen. The electrodes were then immersed in a 0.2–0.5 M cystamine dihydrochloride 104 solution for 2 hours, then introduced into distilled water for 15 mins. and dried with nitrogen. This gave rise to formation of a cystamine monolayer 106 on electrode 102. This gave rise to a resonance frequency change ($\Delta f$) within the range of $\Delta f=(-200)-(-500)$ Hz, as can be seen in FIG. 5, which shows the $\Delta f$ change with time of incubation in cystamine.

Figure 6:
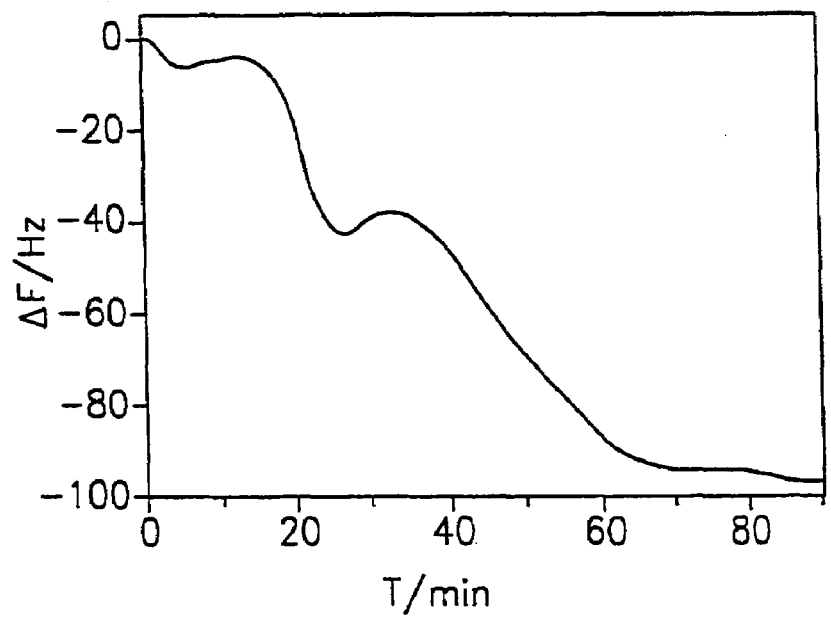
FIG. 6 shows the frequency changes (T/min denotes Time in minutes) of the crystal during the process of binding of the capturing agent to the system in monolayer.

2-5-Dinitrosalicylic acid was dissolved in a HEPES buffer solution (0.01 M, pH=7.4) to yield a 0.15 M solution. As solubilization of 2,5-dinitrosalicylic acid is slow, it was assisted by sonication. 0.1 M EDC (1-ethyl-3-(3-dimethylamino propyl)carbodiimide and 0.1 M NaNHS (N-hydroxysulfosuccinimide sodium salt) were dissolved in the antigen solution. The cystamine-modified electrodes 106 (see FIG. 4) were incubated in this solution for two hours to yield an antigen-cystamine monolayer 108 immobilized on electrode 102. This yielded a typical $\Delta f$ of the crystal of about −100 Hz (FIG. 6).

Figure 7:
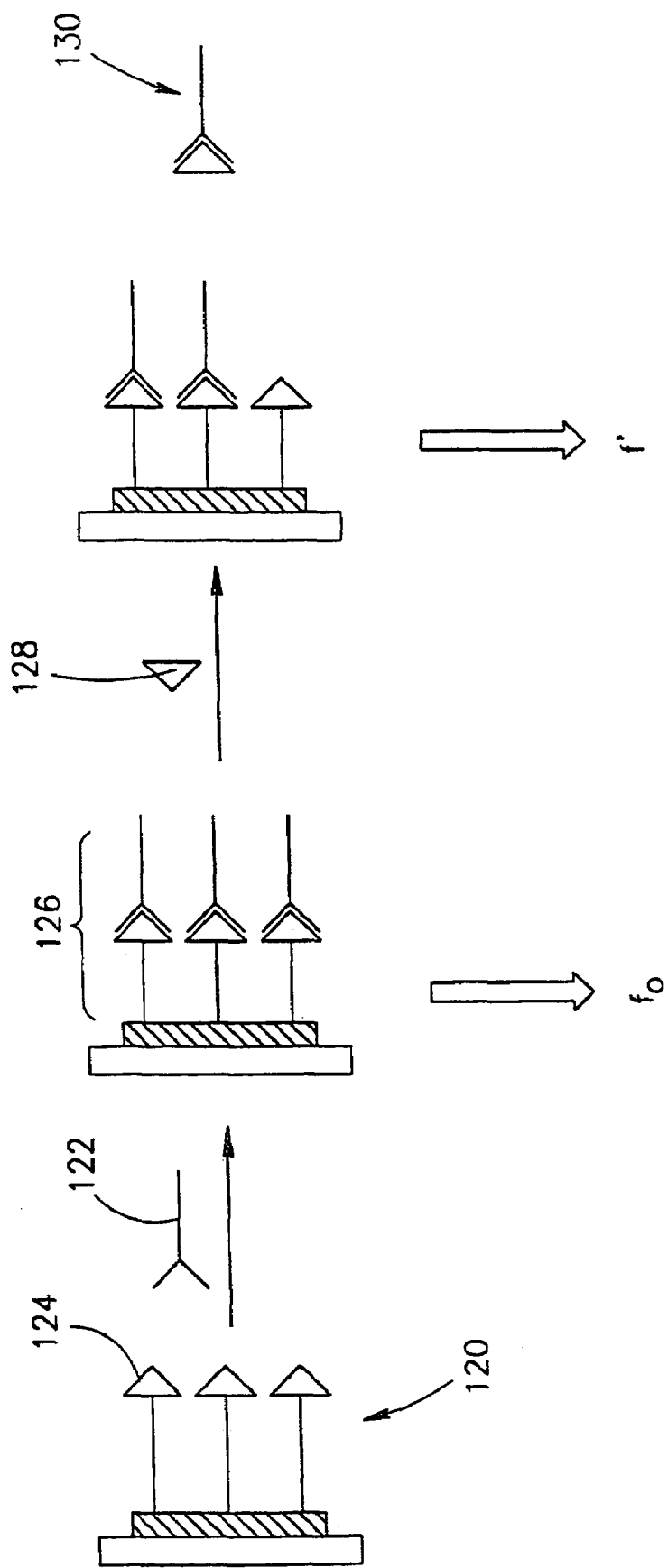
FIG. 7 is a schematic illustration of a basic configuration of the displacement embodiment.

3. Analysis of Small Molecules in Accordance with the Displacement Method 3.1 General Outline of the Displacement Embodiment The scheme for analysis of a small assayed molecule is illustrated schematically in FIG. 7. The antigen monolayer 120 is contacted with an antibody 122 which then binds to the antigen moieties 124 to yield an antigen-antibody monolayer 126. Measurement of resonance frequency at this stage yields a certain basic frequency $f_o$.

Challenging the electrode with a sample comprising antigens 128 causes release of some of the antibodies 122 to yield a soluble antigen-antibody complex 130. This reduces the immobilized mass and consequently the frequency is increased as a result of this antibody displacement to a certain frequency f. The decrease in frequency is a result of and signifies the presence of the assayed molecule 128 in the medium; the extent of the frequency change depends on the concentration of the assayed molecule in a sample.

3.2 Assay Apparatus

Figure 8:
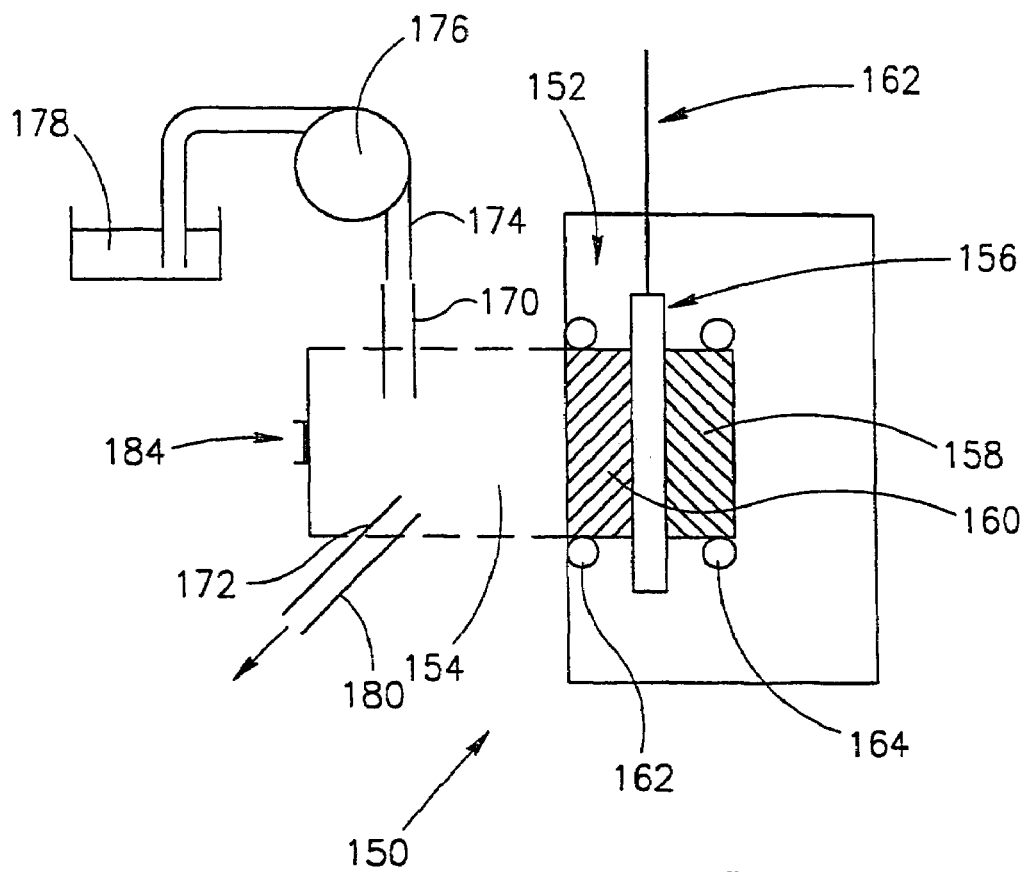
FIG. 8 is a schematic, more detailed illustration of a measuring cell with the sensing measure in accordance with an embodiment of the invention.

An assay apparatus generally designated 150 is shown schematically in FIG. 8. The apparatus 150 comprises a sensing member 152 and an analysis cell 154. The sensing member 152 consists of the quartz crystal 156 sandwiched between two gold electrodes 158 and 160 which are connected through connector 162 to a control utility (not shown) for inducing current in electrodes 158,160 and measuring the resonance frequency of crystal 156.

Sensing member 152 is sandwiched between two O-rings 162 and 164 and has one electrode 160 which faces cell 154. Electrode 160 serves also as the sensing surface of sensing member 152.

Cell 154, typically having a volume of 1 ml or less, has entry and exit ports 170 and 172, respectively which allow rinsing of cell 154. Inlet port 170 is connected through duct 174 to a peristaltic pump 176 which pumps fluid from reservoir 178 into cell 154; outlet port 172 is connected to a duct 180 which drains fluid to a drain (not shown).

Cell 154 has also a liquid injection port 184 for injection of samples to be assayed. As will no doubt be appreciated, rather than injection port, the cell may comprise another port which will permit propelling of a liquid into the cell directly from a specimen sampling device (not shown).

3.3 Assaying of Samples using the Apparatus of FIG. 8

The sensing member is mounted in the cell, the cell volume is filled with a solution, e.g. 0.01 M phosphate buffer, pH 7.4 comprising also 0.1 M NaCl ("NaCl-containing PBS"). The sensing member is allowed to equilibrate until a constant frequency of the crystal is observed.

The sensing surface in accordance with this embodiment, where the neutralizing agent is an antibody, comprises an antigen-antibody monolayer. Electrode 160 may be provided, a priori with antibodies bound thereon, although alternatively, the antibody may be bound to the sensing surface in situ. In the latter case, an antibody solution, e.g. 50 µl of a 1 mg/ml antibody solution is injected into the cell and permitted to incubate with the electrode for a time to allow binding, e.g. 15 minutes. Association of the antibody to the electrode can be monitored by the decrease in the resonance frequency of the crystal (see FIG. 9 and the accompanying description below). The cell may then be rinsed with several cell volumes of a solution, e.g. a buffer solution, propelled by means of peristaltic pump 176. The electrode is then allowed to calibrate until the resonance frequency remains constant for a period of time.

Figure 10:
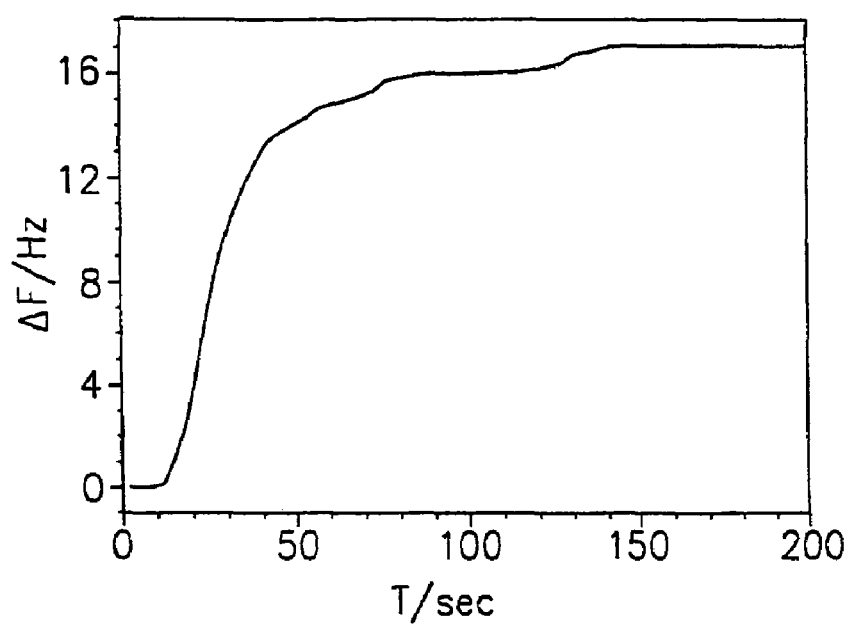
FIG. 10 shows the crystal frequency changes (T/min denotes Time in seconds) during incubation of the DNP-Ab containing layer with a medium comprising 2,4-DNT.

Samples may then be injected into the cells. Detachment of the antibody from the monolayer is evidenced by a frequency increase of the crystal (see exemplary FIG. 10 and the accompanying description below). After each positive sample the cell is flushed with a buffer solution and allowed to re-equilibrate to reach a constant frequency.

It was found that usually a single electrode can be used consecutively for several positive samples, e.g. three positive samples. After several positive samples, the antibody monolayer has to be reformed.

In the specific example of the antibodies which will be described below, it was found that three positive 2,4-DNT samples in the concentration range of about 0.3–7 ng/ml can be analyzed with a single electrode prior to the need to recharge the electrode with antibodies. With the same antibody interface, typically three TNT positive samples in the concentration range of 6–65 pgr/ml can be analyzed with a single electrode prior to the need for recharging. A single electrode can typically be recharged several times, e.g. three, until the sensing member has to be changed. It should be noted that in typical use, most samples are expected to be negative and thus the requirement to occasionally recharge the electrode or change the sensing member is not a serious drawback.

3.4 Analysis of 2,4-DNT

Figure 9:
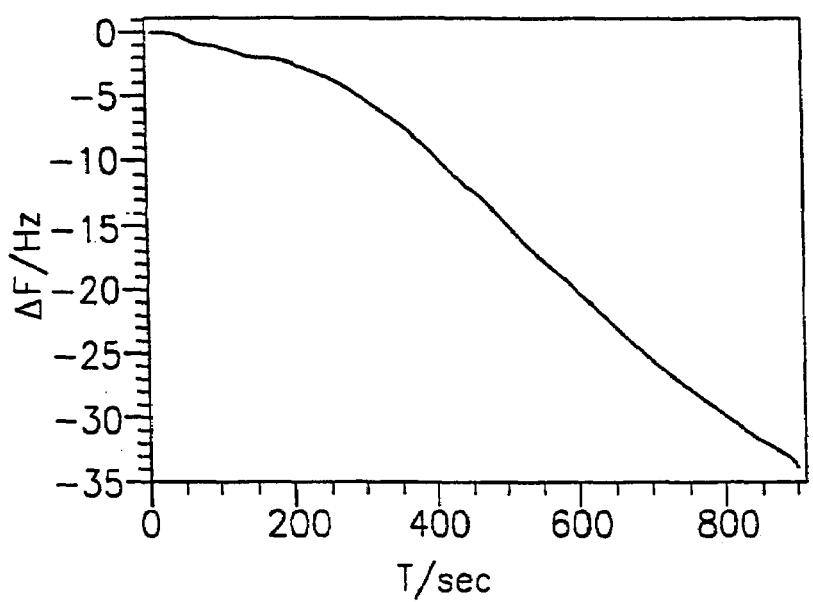
FIG. 9 shows the resonance frequency decrease (T denotes Time in seconds) of the crystal upon association of the anti-DNP antibodies ("DNP-Ab") to the sensing surface.

DNP-Ab was charged on the antigen monolayer as described above. FIG. 9 shows the crystal frequency decrease upon association of the anti-DNP antibodies (DNP-Ab) to the monolayer. To obtain full charging of the monolayer, the electrode was interacted with the DNP-Ab for 15 minutes. The cell was then rinsed with the buffer solution.

2,4-DNT was dissolved in ethyleneglycol monomethyl ether, 100 µl and diluted with the NaCl-containing PBS to 1 ml. The solution was diluted repeatedly with the buffer solution to the desired concentration.

Injection of 2,4-DNT sample (50 µl) to the cell, that yields in the cell a concentration of 2,4-DNT of about 20 ng/ml$^{-1}$, displaces the DNP-Ab. This can be seen in FIG. 10 which shows the crystal frequency changes following such injection of 2,4-DNT. A frequency increase of about $\Delta f=16$ Hz was observed.

3.5 Analysis of 2,4-DNT by IgG TTDA 5B3-Ab

Figure 11:
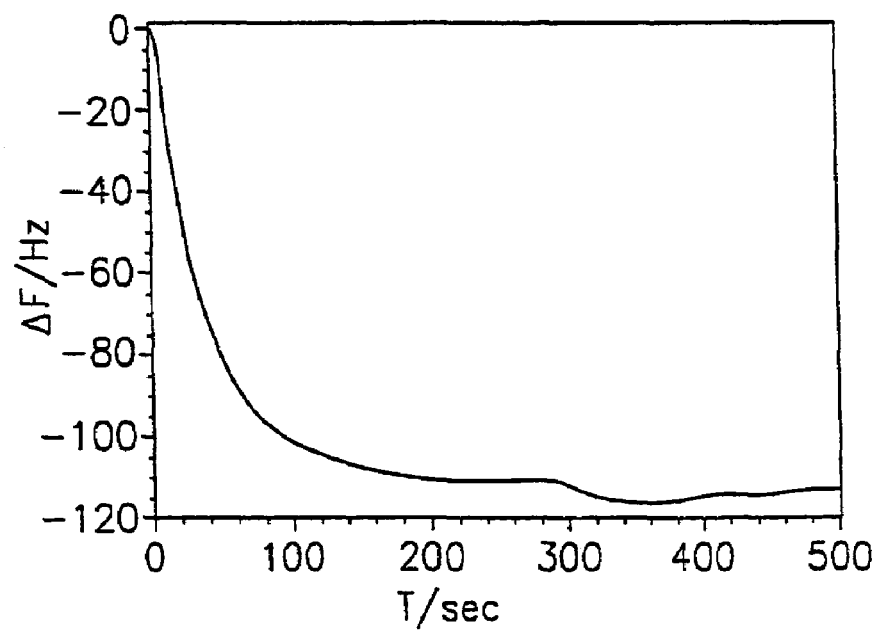
FIG. 11 shows the decrease in the crystal's resonance frequency (T/sec denotes Time in seconds) upon binding of the mAb 5B3 to a cystamine/3,5-dinitrosalicylic acid monolayer.

An antigen monolayer electrode was treated for 15 mins. with the Ab. FIG. 11 shows the crystal frequency decrease upon saturation of the monolayer. A decrease of about $\Delta f=-100$ Hz was observed. The charged electrode was rinsed for 3 mins with the buffer solution and its resonance frequency was stabilized.

Figure 12:
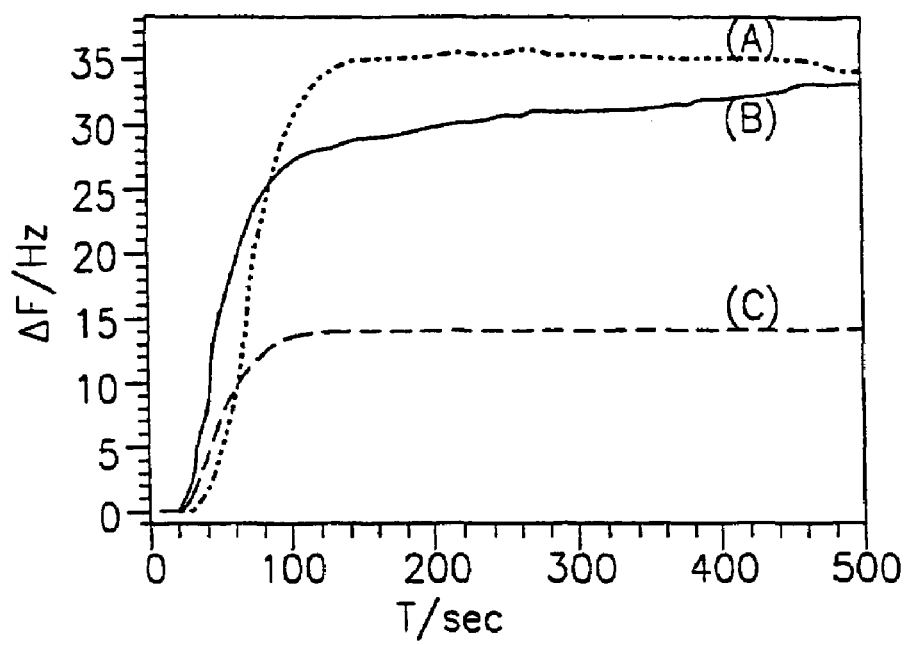
FIG. 12 shows the increase in frequency (T/sec denotes Time in seconds) of the crystal of FIG. 11 upon injection of 2,4-DNT to the cell at a concentration of 6.25 ng/ml (curves A and B) and 312 pgr/ml (curve C).

50 ml of stock solution of 2,4-DNT, prepared as described under 3.4 was injected into the cell to yield the desired concentration. The crystal frequency increased by about $\Delta f=-35$ Hz upon injection of 2,4-DNT to a concentration of 6.25 ng/ml into the cell, as can be seen in FIG. 12 (curve a).

The electrode was then rinsed for three mins. with the buffer solution and its frequency was re-stabilized. A sample of 2,4-DNT was injected again into the cell to yield the sum concentration of 6.25 ng/ml. A frequency increase of about $\Delta f=-30$ Hz was observed as can be seen in FIG. 12 (curve b). The electrode was rinsed again and its frequency was stabilized. A 2,4-DNT sample was injected into the cell to yield a concentration of 312 pgr/ml. The crystal frequency increases again by about $\Delta f=-15$ Hz, as can be seen in FIG. 12 (curve c).

This example shows that the antigen monolayer electrode charged with the Ab is reusable for at least three positive samples of 2,4-DNT.

3.6 Analysis of TNT by IgG TTDA 5B3-Ab Interface 3.6.1 Repeated Assaying of TNT

An electrode of a sensing member was charged with Ab in an identical manner to that described under 3.5.

Figure 13:
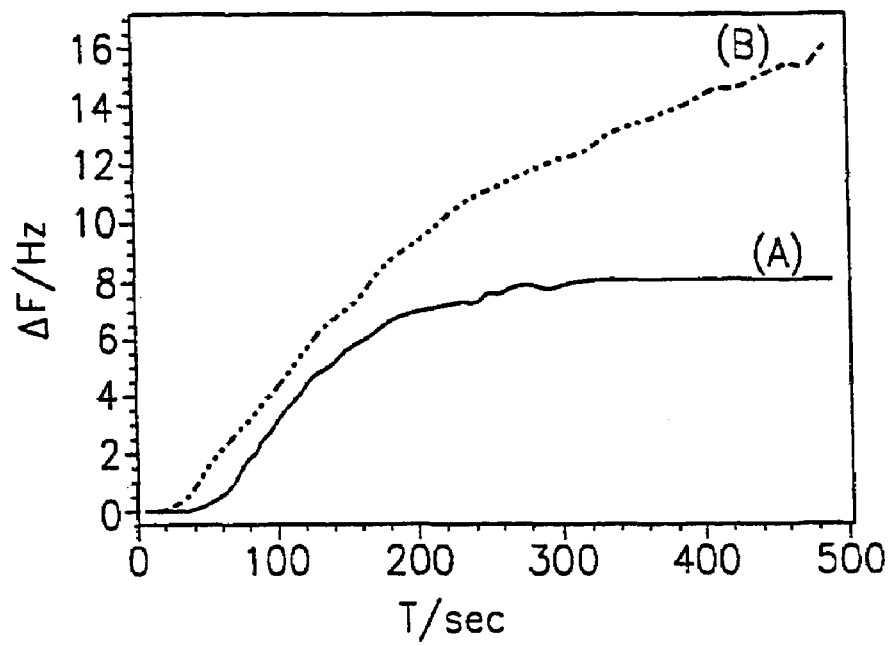
FIG. 13 shows the frequency increase (T/sec denotes Time in seconds) upon injection of TNT at a concentration of 6.25 pgr/ml (curve A) and 62.5 pgr/ml (curve B), of the sensing member of the kind used in FIG. 12.

A TNT stock solution was prepared similarly to the manner of preparation of the 2,4-DNT stock solution in Example 3.5. A 50 ml sample of the TNT stock solution was injected into the cell to yield a concentration of 6.25 pgr/ml in the cell. This resulted in a time-dependent frequency increase of up to about $\Delta f=7$ Hz (FIG. 13, curve a). After rinsing the cell and stabilization of the crystal frequency, a second sample of TNT was injected to the cell, yielding a concentration of 62.5 pgr/ml$^{-1}$. This resulted in a time-dependent frequency increase of the crystal up to about $\Delta f=16$ Hz (FIG. 13, curve b).

The analysis of TNT can be repeated for at least three times after charging the monolayer with the Ab.

This example demonstrates the possibility of reusing the electrode for at least three samples of TNT in this concentration range.

3.6.2 Recharging of the Monolayer with IgG TTDA 5B3-Ab

Figure 14:
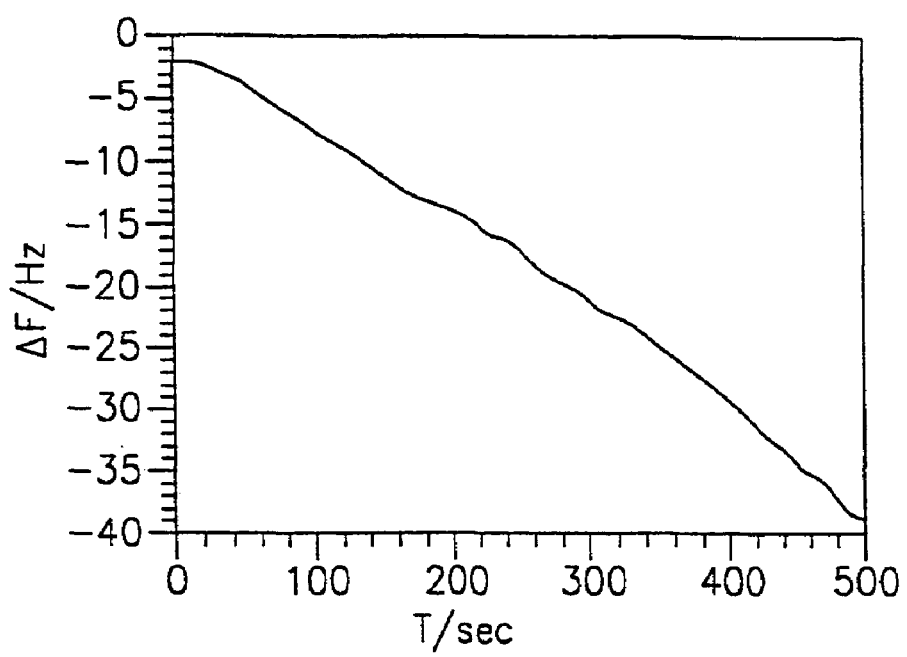
FIG. 14 shows the resonance frequency decrease CT/sec denotes Time in seconds) of the electrode employed in FIG. 13, upon recharging the monolayer with the 5B3 antibody.
Figure 15:
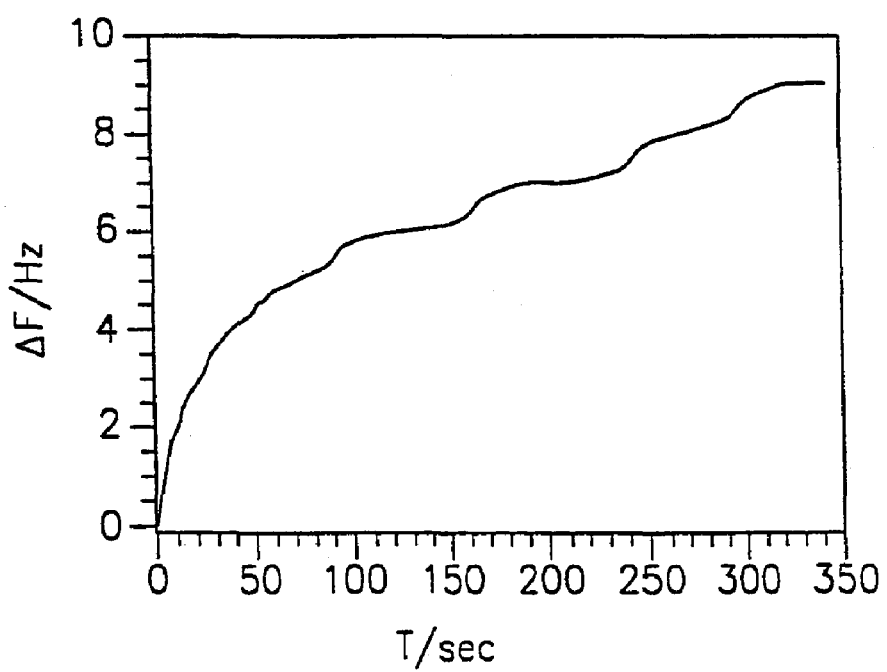
FIG. 15 shows the frequency increase (T/sec denotes Time in seconds) of the electrode of FIG. 14, upon contact with a sample containing 6.25 pgr/ml TNT.

The monolayer electrode employed for the analysis of two consecutive TNT samples (6.25 and 62.5 pgr/ml$^{-1}$, respectively) was rinsed and recharged with IgG TTDA 5B3 Ab (see FIG. 14) as described in Example 3.6.1. FIG. 15 shows the crystal frequency increase upon treatment of the electrode with a TNT sample, at a final concentration within the cell of 6.25 pgr/ml. A frequency increase up to about $\Delta f=18$ Hz was observed indicating that the Ab was displaced from the interface as a result of the presence of TNT in the sample.

This example demonstrates the possibility of recharging the electrode with the Ab and regenerating the active interface for TNT/DNT analysis.

3.7 Amplification of 2,4-DNT Detection by DNP-Ab

Figure 16:
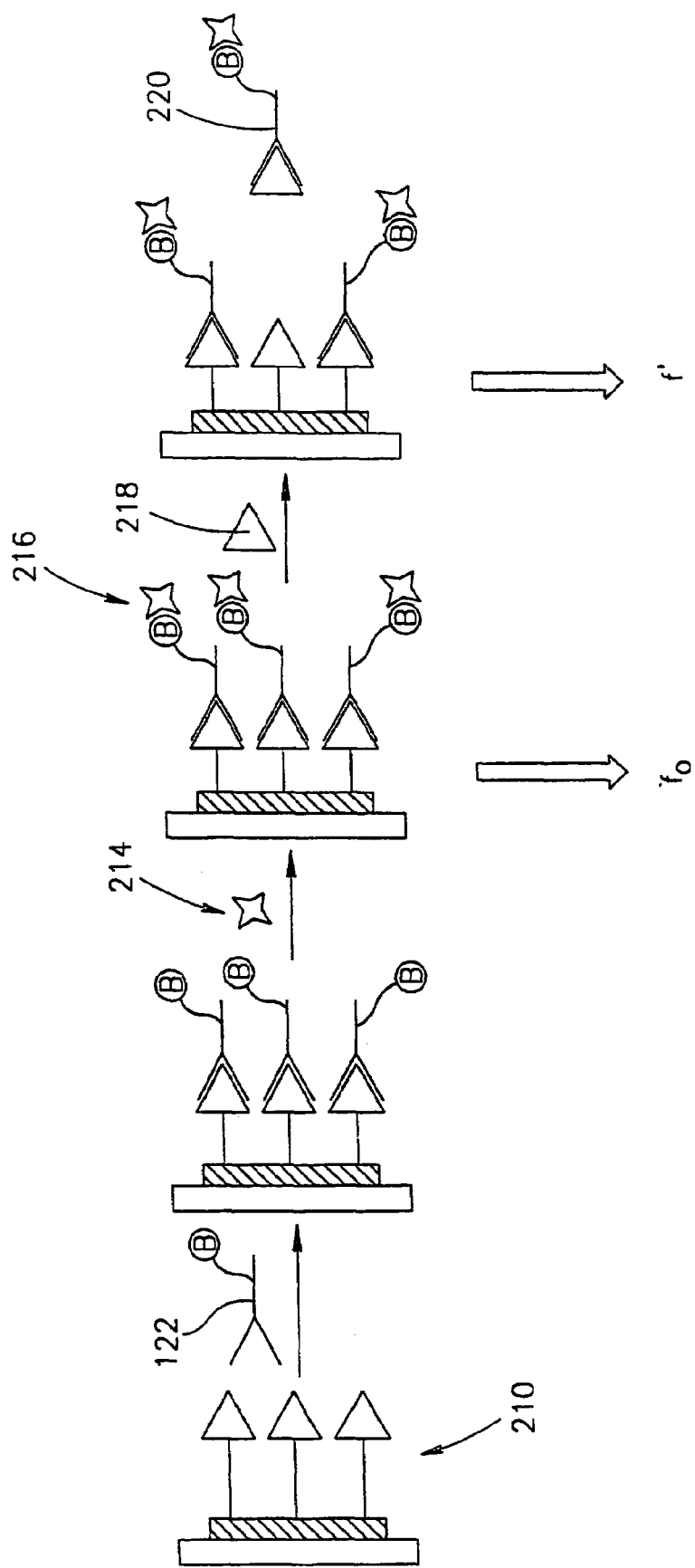
FIG. 16 is a schematic illustration of a configuration of the displacement embodiment wherein a mass-increasing agent is used.

The concept for the amplification of DNT/TNT analysis is schematically outlined in FIG. 16. The antigen monolayer-modified crystal 210 is fictionalized by a biotinylated DNT/TNT-Ab 212. Avidin 214 is further linked to the monolayer yielding an Ab-avidin complex monolayer 216 on the crystal. Challenging the functionalized electrode with a DNT/TNT antigen 218 results in the displacement of the Ab-avidin complex 220 from the monolayer as a result of binding to the analyte-antigen. The increased mass of the dissociated material from the monolayer allows the detection of minute quantities of displaced Ab and consequently the sensitivity of the analysis of DNT/TNT is enhanced. (The difference, $\Delta f$, between the basic resonance frequency, $f_o$ and that after dissociation, f will increase.

As will be appreciated, this example of assaying the explosive TNT or DNT is a mere illustration of the more general concept of assaying small molecules, which may be other explosive molecules as well as non-explosive molecules.

3.7.1 Preparation of Biotinylated DNP-Ab 0.5 mg of the DNP-Ab was introduced into 1 ml of the NaCl-containing PBS. 5 mg Biotinamidocaproate N-hydroxy-succinimine ester, was added to the mixture. The solution was mixed at room temperature for 1 hour and then dialyzed against the NaCl-containing PBS for 15 hours. Dialysis was performed at 0° C. The resulting 7.5 ml dialyzed antibody solution was concentrated to 2 ml using an Amicon™ (Amicon, U.S.A.) filter.

3.7.2 Charging of the Antigen Monolayer with the DNP-Ab-avidin Complex

Figure 17:
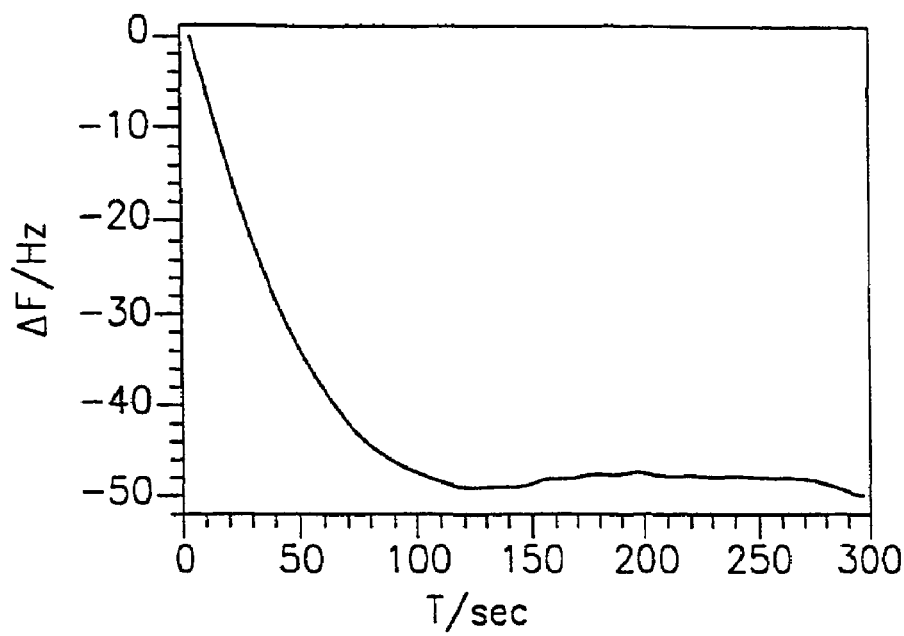
FIG. 17 shows the decrease in resonance frequency of a crystal (T/sec denotes Time in seconds), upon addition of biotinylated antibody to the antigen monolayer on the sensing surface.

The antigen monolayer electrode was charged with the 0.1 mg/ml biotinylated DNP-Ab as described in Example 3.4 After charging of the electrode with the Ab, the cell was rinsed with a PBS (0.01 M, pH=7.4) buffer solution for 3 mins. The electrode frequency was then stabilized and 50 µl of a 0.01 M avidin solution in the PBS buffer were injected into the cell. FIG. 17 shows the crystal frequency changes upon association of the biotinylated Ab to the antigen monolayer. A frequency decrease of about $\Delta f=-50$ Hz was observed.

Figure 18:
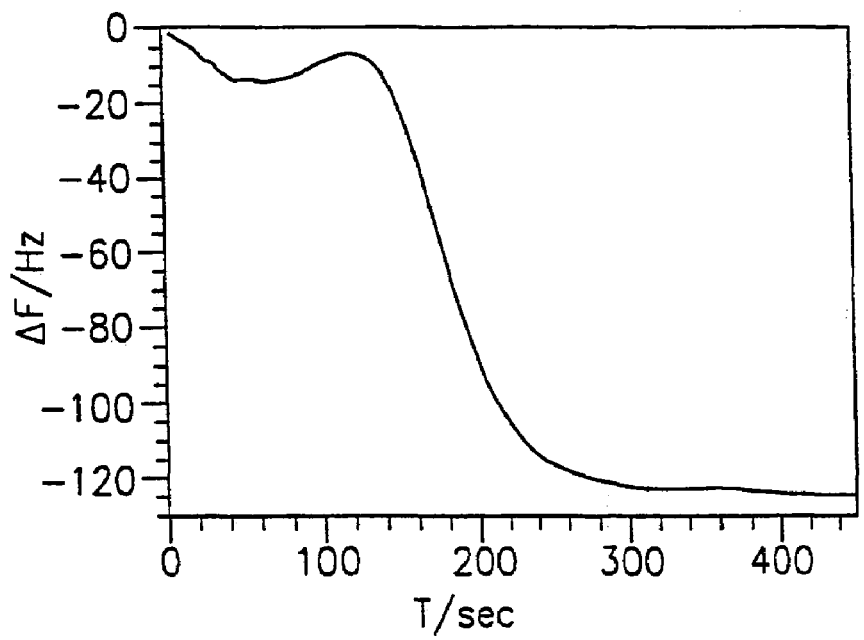
FIG. 18 shows the time-dependent frequency decrease (T/sec denotes Time in seconds) of a crystal charged with biotinylated antibodies, upon interaction with avidin.

FIG. 18 shows the time-dependent frequency decrease of the crystal charged with the biotinylated Ab upon interaction with avidin. The crystal frequency decreases by about $\Delta f=-120$ Hz, indicating the formation of the Ab-avidin complex on the monolayer. The resulting charged electrode was rinsed with PBS and the crystal frequency was stabilized.

Figure 19:
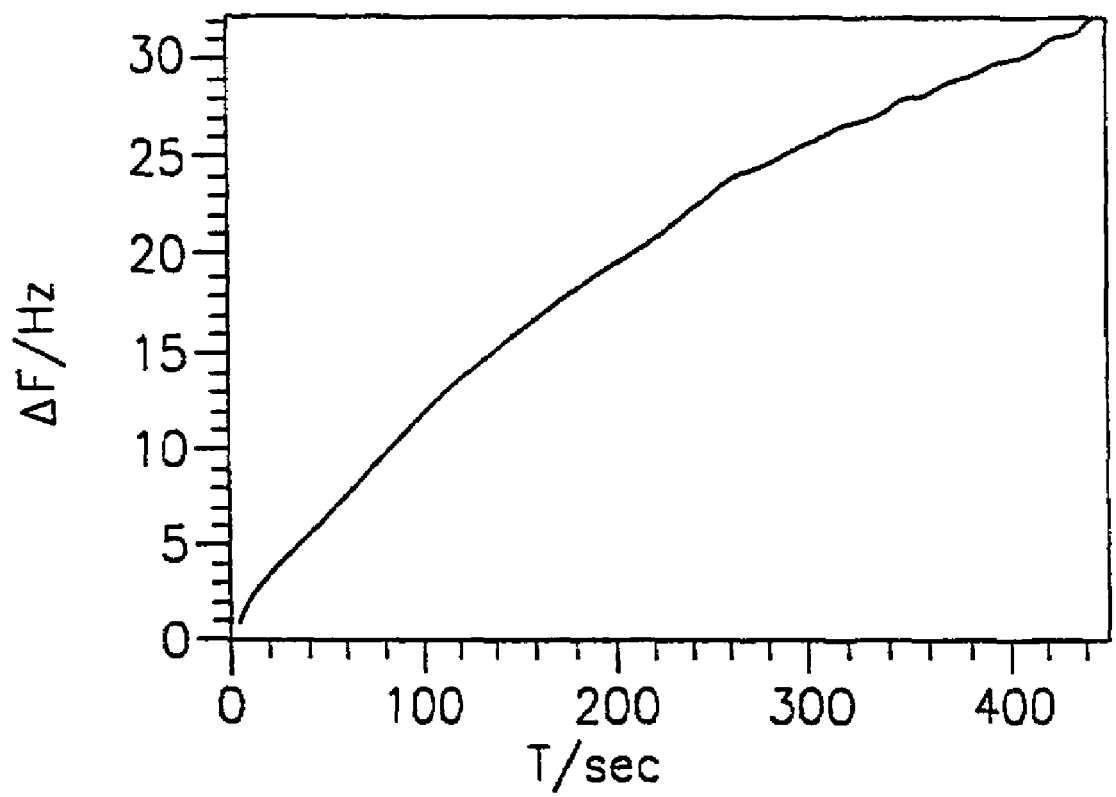
FIG. 19 shows the crystal resonance frequency increase (T/sec denotes Time in seconds) upon exposure of a sensing surface containing a DNT-antibody-avidin layer to a 2,4-DNT sample.

3.7.3 Analysis of 2,4-DNT by the Electrode Functionalized by the Ab-avidin Complex Monolayer A stock solution of 2,4-DNT was prepared as described in Example 3.4. A 50 ml sample of the 2,4-DNT stock solution was injected into the cell to yield a concentration of 2.7 ng/ml within the cell. FIG. 19 shows the crystal frequency increase upon interaction of the electrode that contains the DNP-Ab-avidin layer with the 2,4-DNT sample. A frequency increase of about $\Delta f=30$ Hz is observed, indicating the displacement of the Ab-avidin complex from the monolayer.

It should be noted that a sensor of the kind used in Example 3.4 did not show any frequency increase upon interaction with 2,4-DNT at a concentration of 2.7 ng/ml. The frequency increase of such a concentration is only observed in the presence of the biotinylated Ab-avidin complex, indicating that the complexed Ab-avidin layer enhances the sensitivity of 2,4-DNT detection (about 10 fold sensitivity enhancement as compared to the DNP-Ab monolayer alone).

3.8 Integrated Assay Assembly

Figure 20:
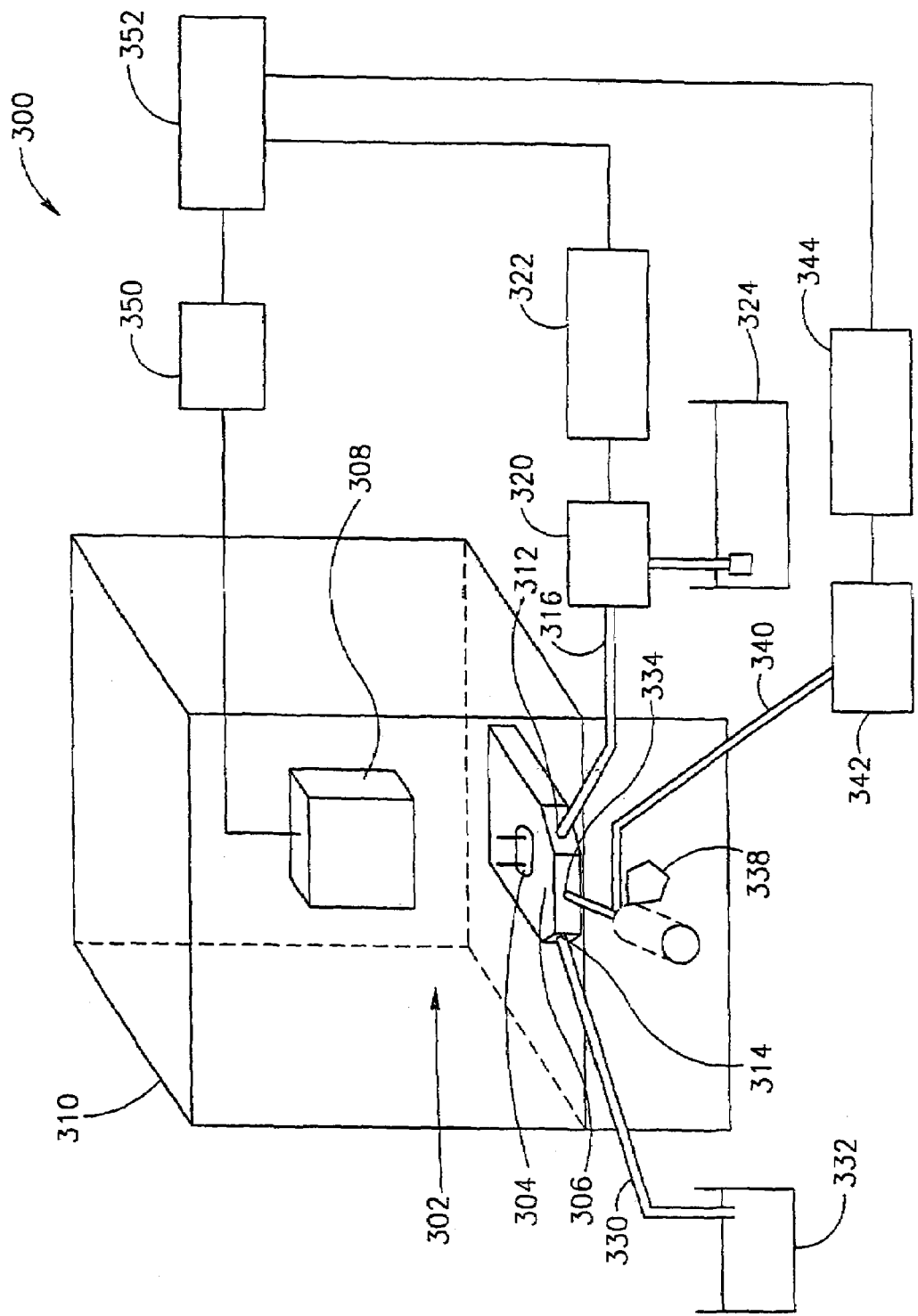
FIG. 20 is a general schematic illustration of a system in accordance with an embodiment of the invention.

An assembly 300 in accordance with an embodiment of the invention, which was used in some experiments reported below, can be seen in FIG. 20. The sensing apparatus 302 is provided with a sensing member 304, with a similar design to that of the apparatus shown in FIG. 8, and an assay cell 306. Sensing apparatus 304 is connectable to an oscillator circuit unit 308, these two components shown here, for the sake of illustration as being detached from one another. Apparatus 302 is included within a Faraday cage 310.

Cell 306 is provided with a fluid inlet port 312 and a fluid outlet port 314. Inlet port 312 is connected to a feedline 316 which is provided with a pump 320 which is under flow control of controller 322. Pump 320 can feed a solution, e.g. a buffer solution, from reservoir 324 into cell 306. Outlet port 314 is connected through ducting line 330 to fluid drain 332.

Cell 306 is further provided with a sample inlet port 334 linked to a three-port injection valve fitted with a 20 µl sample-injection loop 338 (having a design typical to injection loops used in liquid chromatography) which may be linked either to a dispenser line 340, e.g. one fitted with a syringe driver 342 which is controlled by a controller 344. Alternatively, in another embodiment, line 340 may also be linked directly to reservoir 324. The syringe (not shown) of the syringe driver 342 is typically filled with a buffer solution. Oscillator circuit unit 308 is connected to a QCM device 350 linked to a computer 352. Computer 352 is also linked to controllers 322 and 344.

The following are examples of experiments performed in such a system.

3.8.1 Charging of the Electrode in the Micro-Cell

Figure 21:
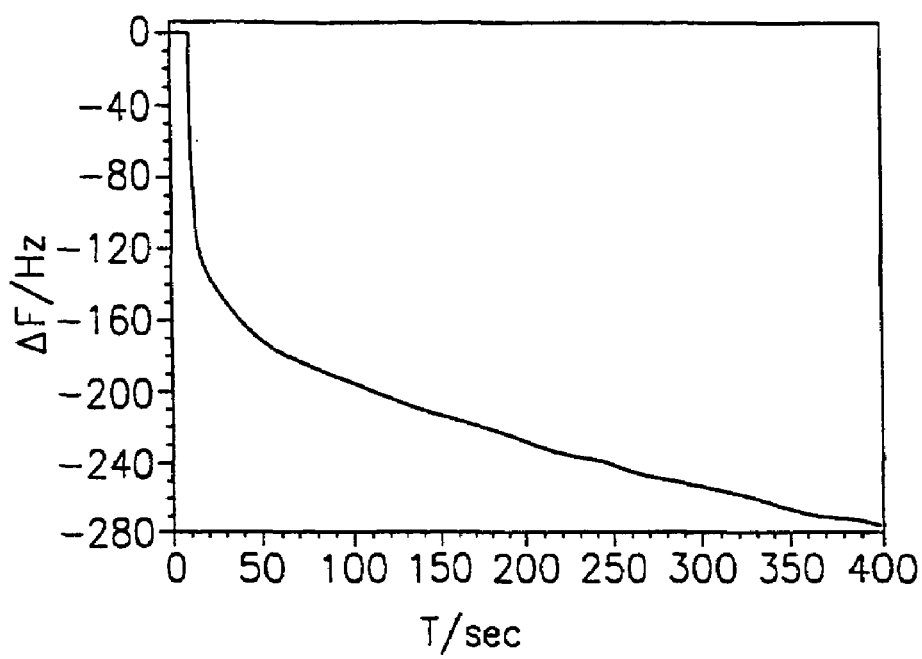
FIG. 21 shows the frequency changes (T/sec denotes Time in seconds) upon interaction of a capturing agent-comprising sensing surface with specific antibodies, in a system of the kind shown in FIG. 20.

The electrode modified by the antigen monolayer was placed in the micro-cell and the cell volume (50 µl) was filled with the NaCl-containing PBS by pumping buffer from the buffer reservoir at a flow rate of 0.5 ml/min. The electrode resonance frequency was allowed to stabilize and the 20 µl injection loop was filled with the 0.1 mg/ml IgG TTDA 5B3 Ab solution. The Ab solution was injected into the cell using the buffer solution in the syringe dispenser to drive out the loop content. 50 µl of the buffer solution were driven by the syringe dispenser at a rate of 60 µl. This volume is that required to drive the Ab solution from the loop and the dead volume of the solution in the connecting pipe into the analyzing cell volume. FIG. 21 shows the crystal frequency changes upon charging the electrode with the Ab. After about 10 mins. of interaction, the electrode was fully charged. The Ab-charged electrode and the injection loop were washed for 4 mins. with a solution from the buffer reservoir, at a flow-rate of 0.5 ml/min., and allowed to equilibrate to a constant frequency. The electrode was then ready for the analysis of DNT/TNT samples.

Figure 22:
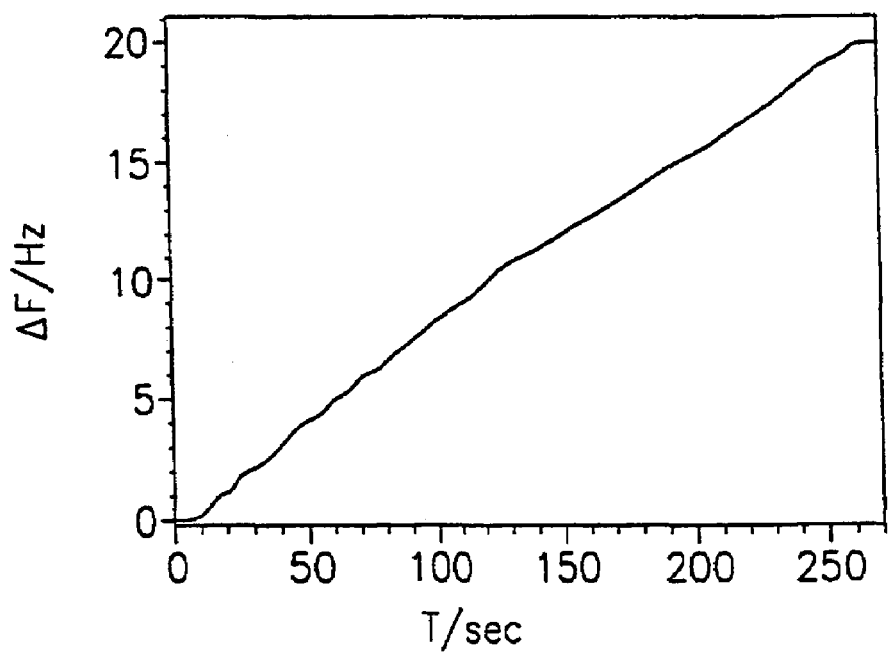
FIG. 22 shows the change in frequency of the crystal shown in FIG. 21 (T/sec denotes Time in seconds), upon exposure to a TNT-containing sample.

3.8.2 Analysis of TNT by the IgG TTDA 5B3 Ab-modified Electrode in the Micro-Cell A 250 pgr/ml TNT sample was prepared by the dilution procedure described in Example 3.6. The 20 µl loop in the injector was filled with the sample. The sample was injected into the cell by the syringe driver using 50 µl of the PBS solution through the loop at a flow-rate of 60 µl/s. As noted above, this volume is that required to drive the loop content into the cell and to overcome the dead volume of the connecting pipe. The final concentration of TNT within the cell was 100 pgr/ml. FIG. 22 shows the time-dependent frequency changes of the crystal as a result of TNT interaction with the electrode. After 3 mins. a frequency increase of about 15 Hz was observed. The frequency increase indicated the displacement of the antibody from the monolayer by the TNT.

After completion of the TNT analysis, the injection loop and the cell were washed for 4 mins. with the buffer solution from the reservoir, at flow rate 0.5 ml/min., and the crystal frequency was re-stabilized, and was ready for another assay sequence. It should be noted that the cell and the loop do not require washing if a non-contaminated sample of suspected TNT is injected into the cell.

4. Analysis According to the Competition Embodiment

In the description below of this embodiment, specific reference will be made to the case where the neutralizing agent is an antibody and the assayed molecule is DNT or TNT. As will be not doubt appreciated this is an example meant to illustrate the invention and should not be construed as limiting.

4.1 Basic Scheme

Figure 23:
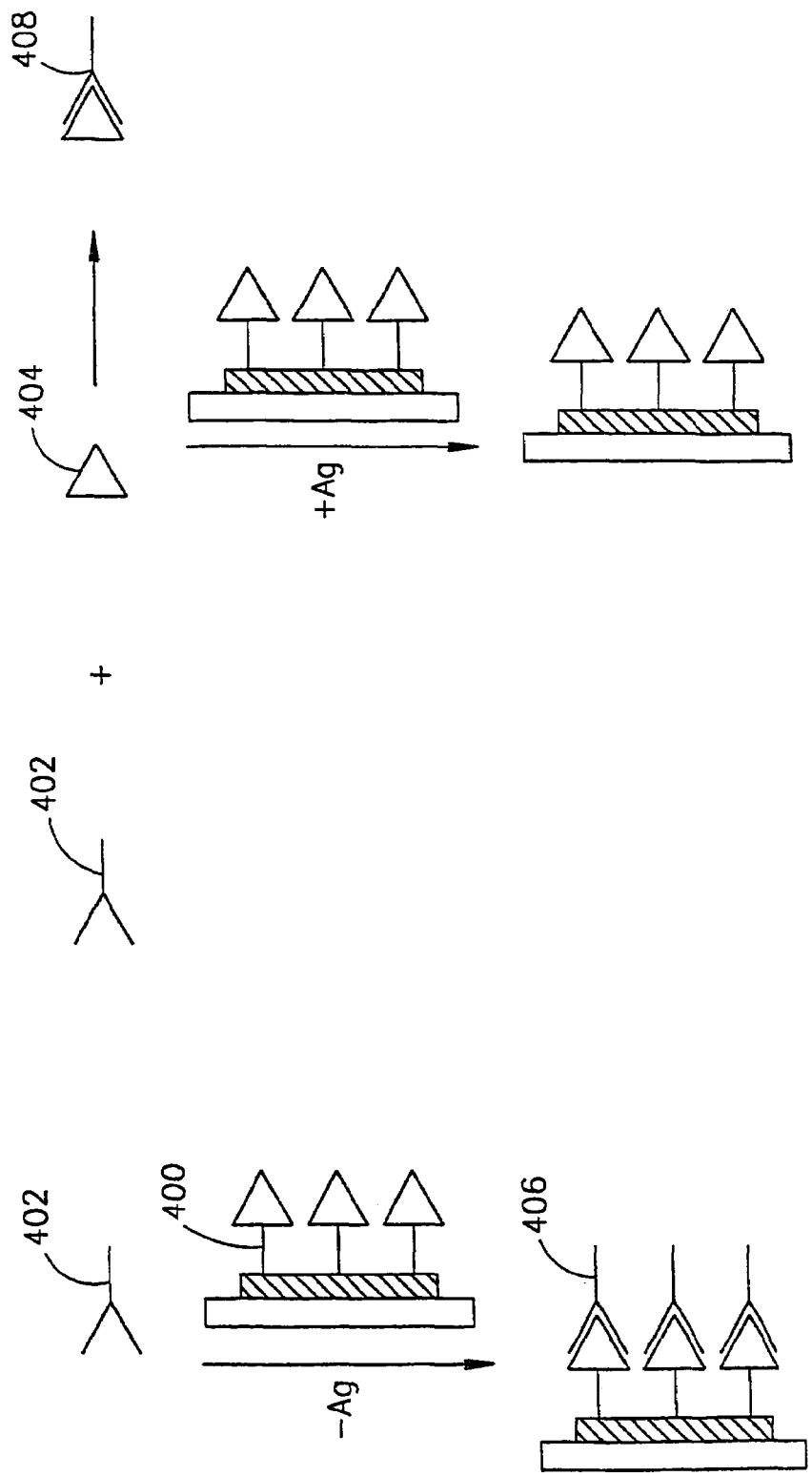
FIG. 23 is a schematic illustration of a basic configuration of the competition embodiment of the invention, in the absence (−Ag) or presence (+Ag) of antigen.

The general scheme of the competition method is displayed in FIG. 23. The quartz crystal is modified with the DNT/TNT antigen monolayer to yield sensing member 400. A stock solution that contains the antibody 402 at a fixed concentration is used as the probe solution. The analyte sample 404 is mixed with the probe solution. In the absence of the DNT/TNT analyte, the antibody remains free, and interaction of the probe solution with the modified crystal results in the association of the free antibody to the antigen monolayer to yield conjugate 406. This results in a frequency decrease of the crystal. Interaction of a sample that includes the DNT/TNT antigen 404 with the antibody probe solution yields the association 408 of the antigen to the antibody. Subsequent interaction of the probe solution with the crystal does not yield the association of the antibody to the monolayer interface, as the antibody is occupied. No frequency change of the crystal will be observed. Thus, a DNT/TNT-free sample induces a frequency decrease of the crystal where a DNT/TNT positive sample does not affect the crystal frequency. It should be noted that preferably, the molar concentration of the antibody in the probe solution must be about 15% lower than the desired molar concentration limit (sensitivity) of the analysis.

4.2 Amplification of the Analysis by the Competition Embodiment

Figure 24:
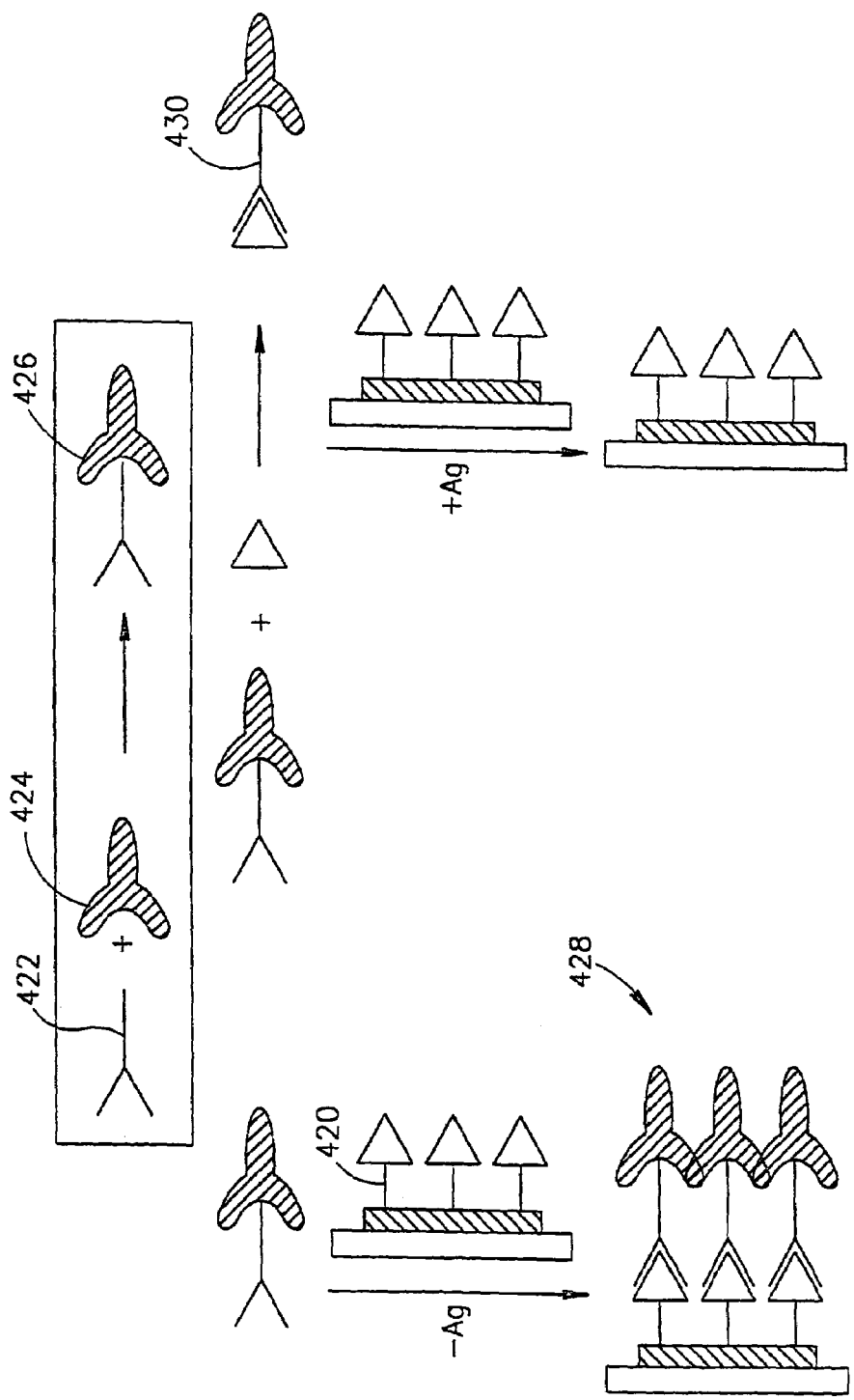
FIG. 24 illustrates a configuration of the competition embodiment, wherein use is made of a mass-increasing agent, in the absence (−Ag) or presence (+Ag) of antigen.

FIG. 24 outlines the principle of the analysis of DNT/TNT through amplification of response obtained in the competition embodiment. The quartz crystal is modified by the DNT/TNT antigen monolayer to yield sensing member 420 (essentially identical to member 400 in FIG. 23). A solution consisting of a fixed concentration of the antibody 422 and a fixed concentration of the anti-antibody 424 which bind to yield conjugate 426 is used as a probe solution. The analyte sample is mixed with the probe solution and incubated for a sufficient time for binding, and then interacted with the antigen-modified crystal. If the analyte sample does not include DNT/TNT, the Ab-anti-Ab complex of the probe solution will associate to the crystal to form immobilized complex 428 resulting in a frequency decrease. Mixing of a positive DNT/TNT sample with the probe solution will generate the antigen-Ab-anti-Ab complex 430 in the probe solution. Interaction of this probe solution with the antigen-modified crystal will not affect the crystal frequency since the sensing Ab is occupied by the antigen. It should be noted that the association of the Ab-anti-Ab complex to the antigen monolayer results in a substantially higher frequency change as compared to that induced by the Ab alone (Example 4.1) since the mass of the associated complex is higher. This allows observation of the higher values of frequency changes and decrease of the concentration of the analyzing Ab in the probe solution. Decrease of the Ab concentration in the probe solution permits to detect lower antigen concentration and to enhance the sensitivity of sensing.

4.3 Experimental Results 4.3.1 Assembly of the Antigen Monolayer on the Quartz Crystals The 3,5-dinitrosalicylic acid was covalently linked to a cystamine monolayer assembled on the Au-electrodes associated with the quartz crystal as described in Example 2.

4.3.2 Antibodies used in the Competition and Amplified Competition Methods

Mouse IgE anti-dinitrophenyl (DNP-Ab) was used as the probe antibody. Goat anti-mouse Fc antibodies were used as the amplifying anti-Ab.

4.3.3 Analysis of 2.4-Dinitrophenol (DNP) by the Competition Method

The configuration of the embodiment is seen in FIG. 24.

A stock solution of 0.3 ng/ml dinitrophenol, in NaCl-containing PBS was prepared. From the stock solution, 10 µl were withdrawn into a vial and 10 µl DNP-Ab solution from $11 \times 10^{-10}$ M stock solution were added to the vial. The mixture was incubated for 15 mins. The total amount of dinitrophenol in the vial was $3.1 \times 10^{-12}$ g. The resulting solution was injected into 1 ml of 0.01 M aqueous phosphate buffer solution, that included 0.1 M NaCl, pH=7.4, were incubated with 10 µl of the $11 \times 10^{-10}$ M DNP-Ab solution. The resulting mixture was injected to the cell solution as described above and the frequency changes of the crystal over time were followed. This reference system does not include the dinitrophenol analyte.

Figure 25:
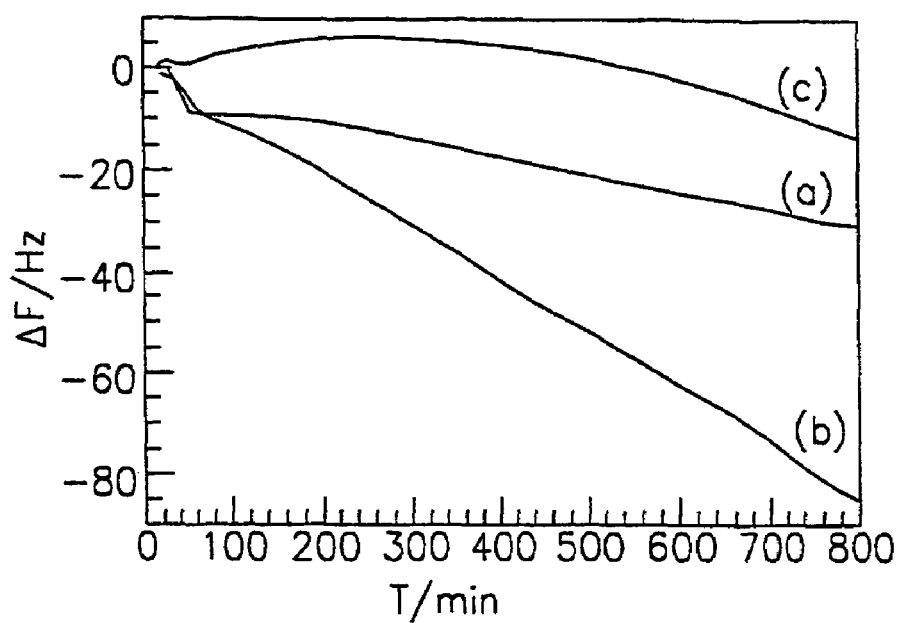
FIG. 25 shows the results of an assay performed in accordance with the competition embodiment (T/min denotes Time in minutes), upon exposure of the sensing surface to a reference system lacking dinitrophenol (curve a), to a DNP-Ab/anti-Ab probe solution lacking the DNP antigen (curve b) and upon exposure to the DNP-Ab/anti-Ab probe solution including $3.1 \times 10^{-12}$ g of DNT (curve c).

FIG. 25 (curve a), shows the frequency changes of the crystal in the reference system lacking dinitrophenol. A frequency decrease of about $\Delta f = -30$ Hz indicates the absence of the analyte in the sample. With the system that includes 3.1 pgr/ml dinitrophenol, a frequency decrease of only (−5.0)–(−8.0) Hz is observed (results not shown) indicating that the probe antibody is occupied.

4.3.4 Analysis of 2,4-dinitrophenol (DNP) by the Amplified Competition Method

A solution of $6.7 \times 10^{-6}$ M DNP-Ab and $6.7 \times 10^{-6}$ M anti-Ab was mixed and incubated for 15 mins. The solution was repeatedly diluted to yield a stock solution of $11 \times 10^{-10}$ M of the DNP-Ab/anti-Ab complex that was used as the probe Ab/anti-Ab solution.

10 µl of a DNP stock solution in an NaCl-containing PBS was incubated with 10 µl of the DNP-Ab and anti-Ab stock solution for 15 mins. The resulting mixture was injected into the cell as described in Example 4.3.3.

In a reference system, 10 µl of the phosphate buffer was mixed with the 10 µl of the DNP-Ab/anti-Ab stock solution and the resulting mixture was injected into the cell as described in Example 4.3.3.

FIG. 25 (curve b), shows the frequency changes of the crystal upon injection of the DNP-Ab/anti-Ab probe solution lacking the DNP antigen. A frequency change of $\Delta f=-85$ Hz is observed, indicating the association of the vacant DNP-Ab/anti-Ab to the crystal interface. FIG. 25 (curve c), shows the frequency changes or the crystal upon injection of the DNP-Ab/anti-Ab probe solution that includes $3.1 \times 10^{-12}$ g of DNP. Only a slight frequency change of about $\Delta f=-12$ Hz, is observed, implying that the DNP-Ab/anti-Ab complex is occupied by the DNP analyte.

4.3.5 Analysis of 2.4-DNT by the Amplified Competition Method using DNP-Ab and Anti-Ab as Probes 10 mg of 2,4-DNT were dissolved in 1 ml of ethylene glycolmonomethyl ether. 100 µl of this solution were diluted to 1 ml with a 0.01 M phosphate buffer solution, pH=7.4, that included 0.1 M NaCl. This solution was repeatedly diluted to achieve the desired concentration of the analyte sample.

A 100 ml of $54 \times 10^{-10}$ M solution of DNP-Ab and anti-Ab were mixed and incubated for 15 mins. to yield the DNP-Ab/anti-Ab probe solution.

Figure 26:
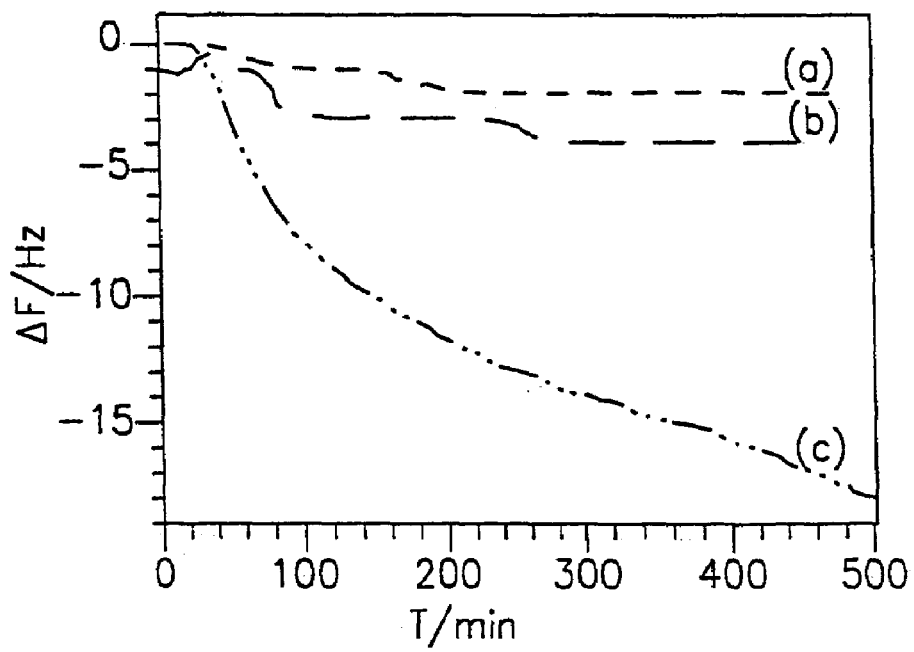
FIG. 26 shows the frequency changes in a crystal of the kind of FIG. 25 (T/min denotes Time in minutes) exposed to DNP-Ab/anti-Ab probe solution mixed with 2,4-DNT (curves a and b) and exposure to a probe solution without 2,4-DNT (curve c).

10 µl of the 2,4-DNT stock solution that included $4.39 \times 10^{-12}$ g of 2,4-DNT were mixed with 10 µl of the DNP-ab/anti-Ab probe solution and incubated for 15 mins. The resulting mixture was injected into the measuring cell that included 1 ml of the phosphate buffer. The frequency change of the crystal as a function of time is seen in FIG. 26, (curve a), showing a final minute frequency decrease of about $\Delta f=-2$ Hz. FIG. 26 (curve b), shows the results of a similar experiment performed for a second time with the same electrode.

As reference system, 10 µl of the phosphate buffer was treated with 10 µl of the DNP-Ab/anti-Ab probe solution as described above. The mixture was then injected into the measuring cell as described for the previous examples. This system lacks the analyte antigen (2,4-DNT) and hence the DNP-Ab/anti-Ab complex stays vacant and is capable of binding to the antigen monolayer of the crystal. FIG. 26 (curve c), shows the crystal frequency changes with time upon injection of this reference solution. The reference solution was injected to the same electrode that was previously employed to twice detect the 2,4-DNT analyte samples. A frequency decrease corresponding to $\Delta f=-18$ Hz was observed, implying that the vacant DNP-Ab/anti-Ab complex associates to the antigen monolayer assembled onto the crystal.

Some conclusions may be drawn from this set of experiments as follows:

(a) A 2,4-DNT-containing sample does not significantly affect the frequency of the crystal. A non-contaminated analyte sample stimulates a frequency change of $\Delta f=-18$ Hz. Any sample showing a frequency change of less than $\Delta f=-5$ Hz may be regarded as a 2,4-DNT contaminated sample.

(b) The method permits successive use of the electrode for 2,4-DNT positive samples. A negative 2,4-DNT sample ruins the electrode since the sensing interface is saturated. After each negative sample, the sensing electrode must be exchanged. This embodiment is particularly useful in the case where a large proportion of the samples are expected to be contaminated with an explosive.

Figure 27A:
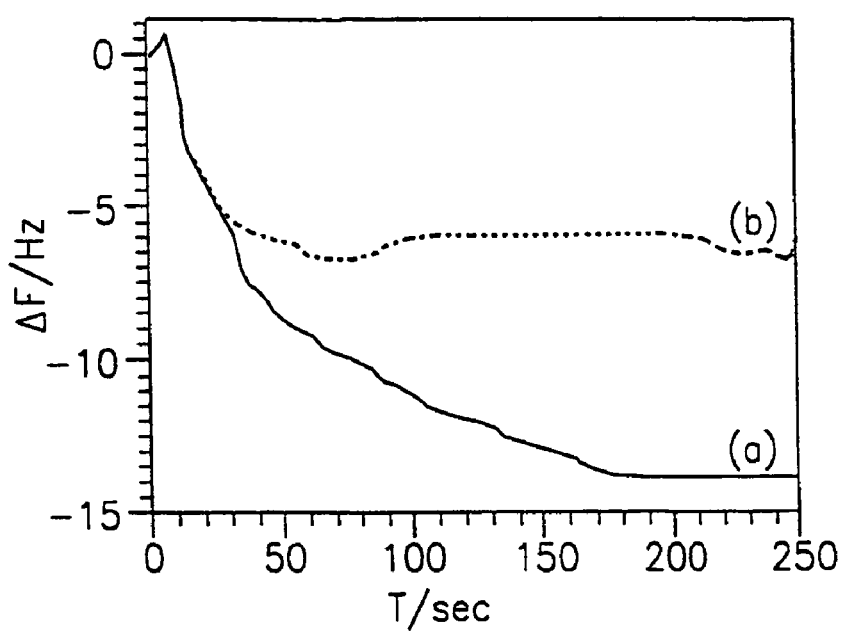
FIGS. 27A–27C show frequency changes of a crystal (in an assay performed in accordance with the competition embodiment, T/sec denotes Time in seconds) upon exposure to different DNT-isomer positive (curve b in the three figures) and in the presence of non-DNT contaminated samples (curves a in the three figures), the isomers being 2,4-DNT in FIG. 27A, 1,4-DNT in FIG. 27B and 2,6-DNT in FIG. 27C.
Figure 27B:
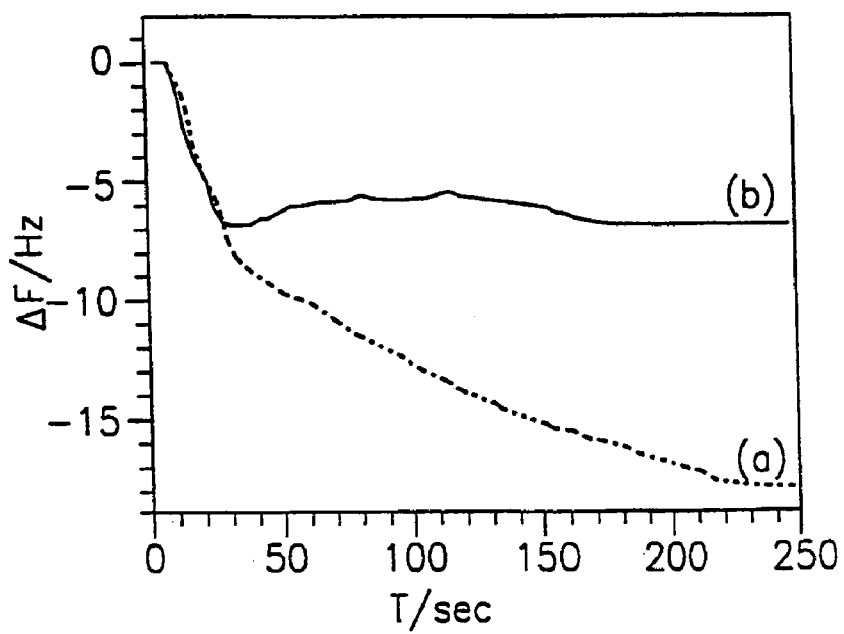
Figure 27C:
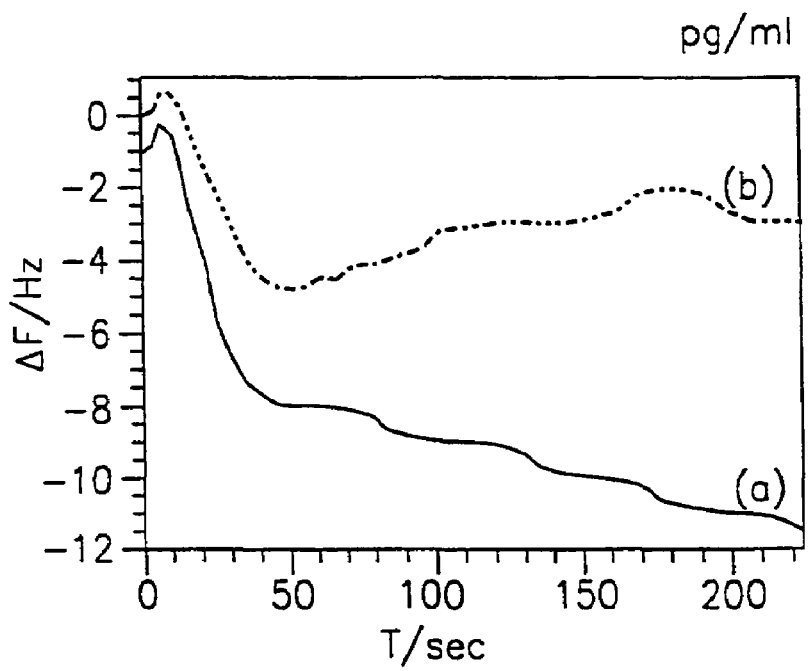

4.3.6 Analysis of DNT-isomers by the Amplified Competition Method using the Dinitrosalicylic Acid Antigen Monolayer and DNP-Ab/anti-Ab as Probe A similar antigen-monolayer-modified crystal was examined as a potential sensing interface for other DNT isomers. The set of experiments described in Example 4.3.5 was performed for 2,4-DNT (78 pgr/ml$^{-1}$), 1,4-DNT (94 pgr.ml$^{-1}$), 2,6-DNT (78 pgr/ml$^{-1}$) and 3,4-DNT (75 pgr/ml$^{-1}$), FIGS. 27A to 27C shows the frequency changes of the crystals in the presence of different DNT-isomer (2,4-DNT, 1,4-DNT and 2,6-DNT, respectively) positive samples (curves a in all these figs.). The frequency changes of the crystals upon their interaction with positive samples of the different isomers, and with the respective reference systems that include the vacant DNP-Ab/anti-Ab probe solution is shown in the following Table 2:

TABLE 2

| Analyte | Concentration pgr/ml | ΔF with analyte | ΔF without analyte |
|---------|----------------------|-----------------|--------------------|
| 2,4-DNT | 78 | −6 | −16 |
| 1,4-DNT | 94 | 07 | −18 |
| 2,6-DNT | 78 | 03 | −12 |

The results reveal that the isomers 2,4-DNT, 1,4-DNT and 2,6-DNT are recognized by the DNP-Ab/anti-Ab probe solution.

A similar experiment with 3,4-DNT indicated that this isomer is not recognized by the DNP-Ab/anti-Ab probe solution. Thus for this isomer a different antibody will be required.

4.3.7 Stability Studies of the Manufactured Antigen-Monolayer-Modified Crystal

A series of 10 crystals that include Au-electrodes were parallel treated in a manner as described in Example 2. The electrodes were dried with an argon and stored under argon at 4° C.

At different time intervals different electrodes were examined for their sensing activity of TNT as analyte and the displacement embodiment as the sensing procedure. The respective electrode was charged with the IgG TTDA 5B3 antibody and 100 pgr/ml of TNT were injected to the cell as detailed in Example 3.

The frequency of the crystal was followed as a function of time to characterize the displacement of the antibody from the sensing interface.

Figure 28A:
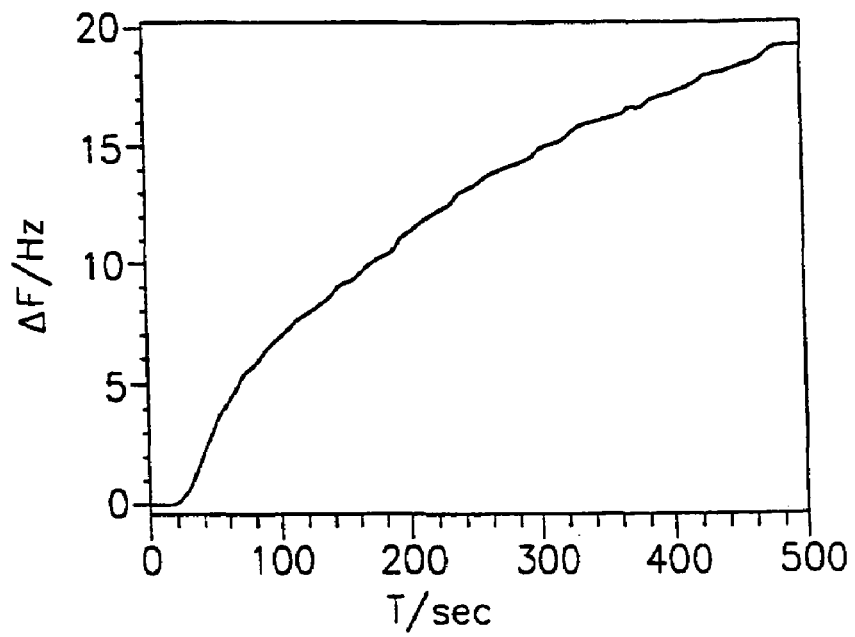
FIG. 28 shows the frequency changes T/sec denotes Time in seconds) of different electrodes which have been stored for 7, 15 and 28 days (FIG. 28A, FIG. 28B and FIG. 28C, respectively), in an assay performed in accordance with the displacement embodiment.
Figure 28B:
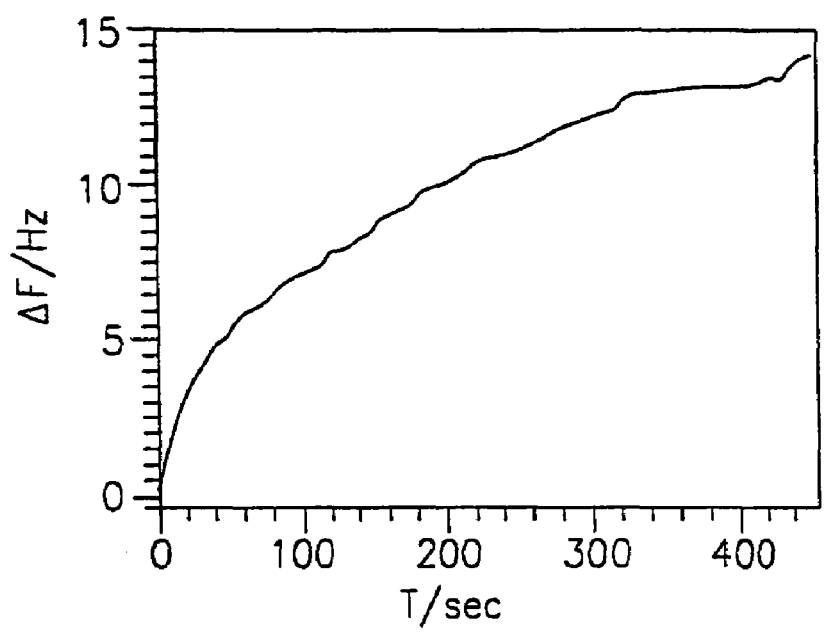
Figure 28C:
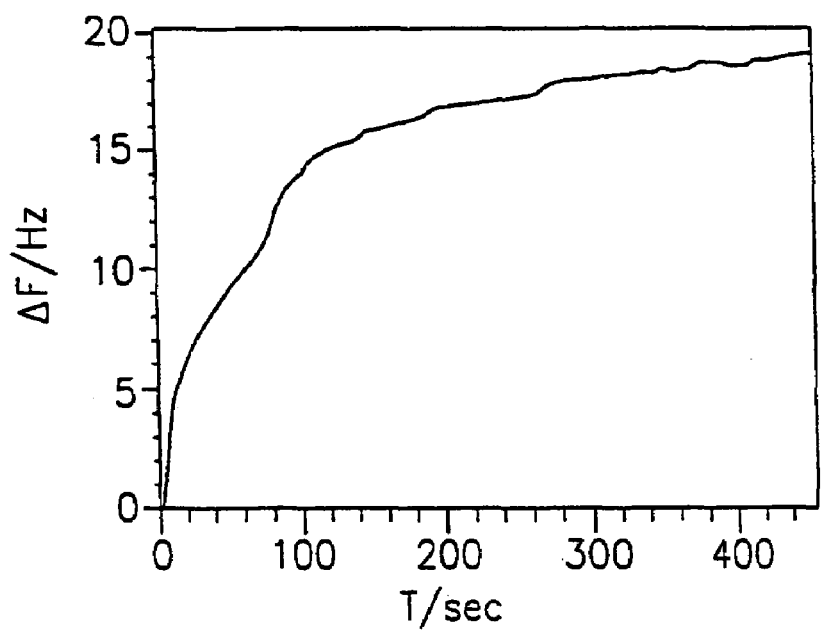

FIGS. 28A–28C show the frequency changes of different electrodes which had been stored for, respectively, 7 days, 15 days and 28 days, with TNT (100 pgr/ml). All of the electrodes reveal comparable activities indicating that the sensing interfaces on the crystals are stable in storage.

Electrodes stored for at least 75 days under the same conditions retained their sensing activities.

5. Analysis of DNT/TNT by the Basic Filtration Embodiment

Figure 29:
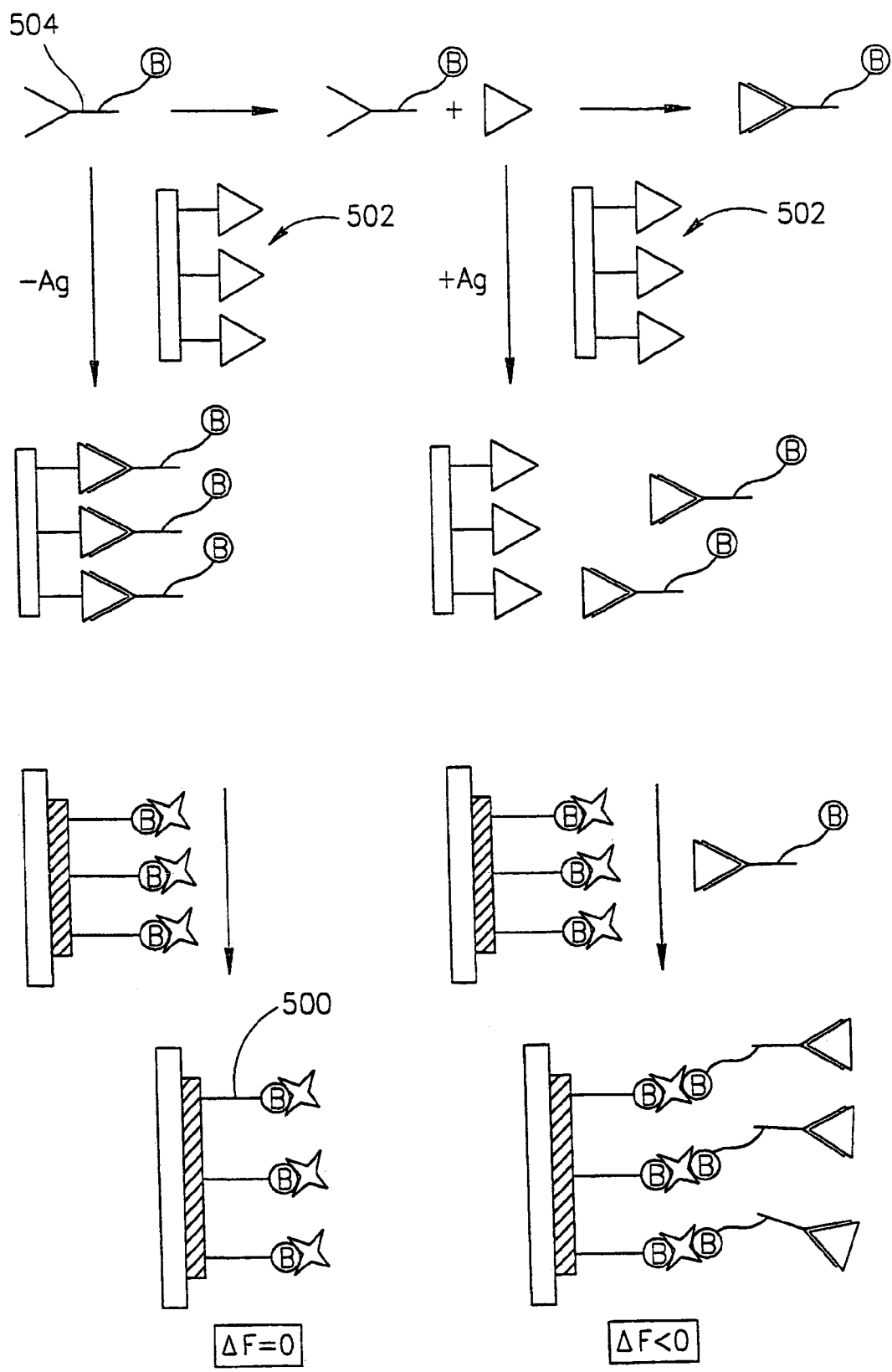
FIG. 29 is a schematic illustrating of the basic filtration embodiment, in the absence (−Ag) or presence (+Ag) or antigen.

This embodiment is outlined generally in FIG. 29.

The quartz crystal is modified by biotin, and avidin is adsorbed to the base monolayer to generate the biotin-avidin sensing interface 500. A filtering support 502 is prepared in the form of an inert solid, coating or filtering material to which the antigen is linked, e.g. by covalent bonding.

The probing antibody is modified by biotin to yield a biotin-functionalized antibody 504. The biotinylated antibody (Ab-B) 506 is solubilized at a fixed concentration to generate the probe solution.

For analysis of DNT/TNT in samples, the ample is first reacted with the antibody probe solution for a time sufficient to ensure binding between the antibodies and the explosive if present in the sample. The probe solution is then passed through or interacted with the filtering support and subsequently introduced into the measuring cell and interacted with the quartz crystal sensing member. As illustrated on the left side of FIG. 29, a clean analyte sample, lacking DNT/TNT, will result in the association of the probe antibody 504 to the filtering support 502. The resulting solution introduced to the cell will lack the Ab-B 504 and the crystal frequency will not change. In the case of a positive DNT/TNT, illustrated on the right side of FIG. 29, the antibody will bind the DNT/TNT antigen. Interaction of the probe solution with the crystal results in the association of the Ab-B to the biotin-avidin monolayer and gives rise to frequency decrease of the crystal.

It is to be noted that the characteristic high sensitivity of the competition embodiment is also a feature of the basic filtration embodiment. Additionally the sensing surface of the crystal is deteriorated only by positive DNT/TNT sample similarly as in the case of the competition embodiment. Furthermore a positive DNT/TNT sample is reflected by a frequency decrease in contrast to the competition embodiment where a positive test does not influence the crystal frequency. This reduces the probability of false positive results of the competition embodiment.

The following are some specific examples of this embodiment.

5.1 Modification of the Quartz Crystal with a Biotin/Avidin Monolayer

Figure 30:
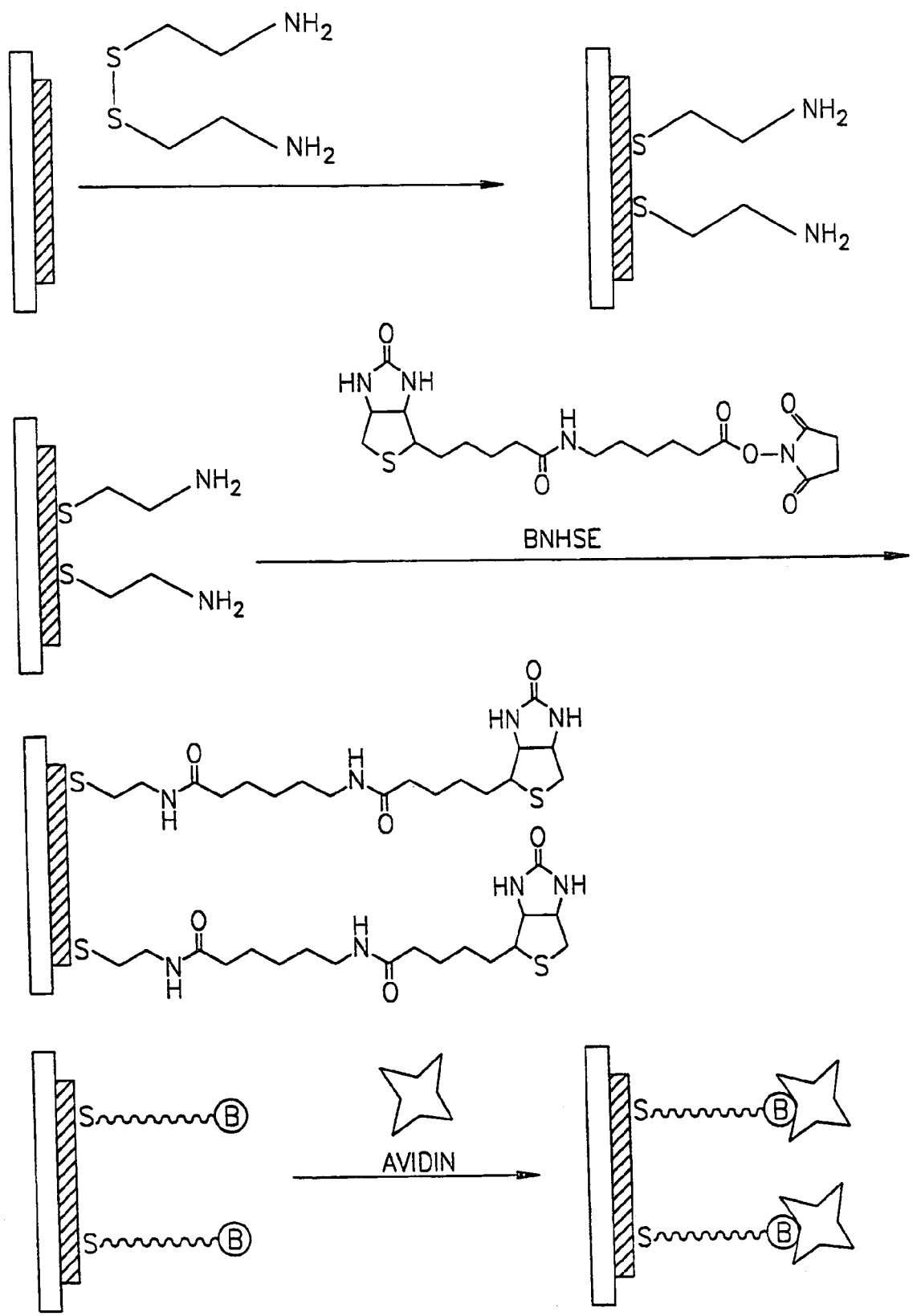
FIG. 30 outlines a step-wise modification of a gold-sensing surface associated with the quartz crystal to obtain a biotin-avidin layer (BNHSE denotes Biotinamidocaproate N-hydroxysuccinimide ester).
Figure 31:
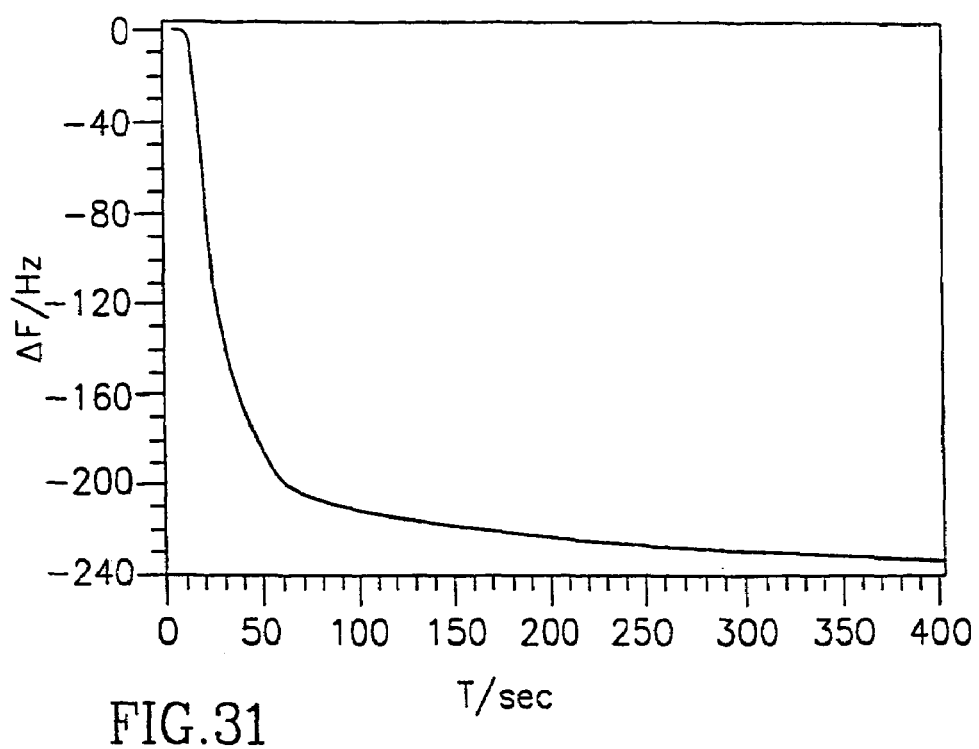
FIG. 31 shows the crystal resonance frequency changes (T/sec denotes Time in seconds) as a result of charging a biotin monolayer with avidin.

FIG. 30 outlines the stepwise modification of the Au-surfaces associated with the quartz crystal to yield the biotin-avidin layer. The Au-surfaces were cleaned and modified by the primary cystamine monolayer as described in Example 2. The cystamine-modified electrode was interacted with an aqueous solution of 0.01 M biotinamidocaproate N-hydroxy-succinimide ester for 1 hour. The resulting biotinylated monolayer-modified crystal was washed, dried and introduced into the measuring cell that included 0.01 M phosphate buffer, pH=7.4. An avidin solution was injected into the cell to yield a concentration of $6.5 \times 10^{-3}$ M in the cell to yield a biotin-avidin monolayer. FIG. 31 shows the resonance frequency change of the crystal with time as a result of the charging of the biotin monolayer with avidin. The cell volume was then washed with the phosphate buffer solution. The system is now charged for analysis of the DNT/TNT analytes.

5.2 Preparation of Filtering Supports

Two different types of filtering supports were prepared:

(a) Glass capillaries, 8 cm in length, 1.5 mm in diameter, were filled with 0.5 M solution of 3-aminopropyltriethoxysilane in toluene and introduced into the same solution. The solution was heated to 85° C. for 15 hours. The resulting capillaries were washed with toluene and then with ethanol and water. The capillaries were then filled with an aqueous phosphate buffer solution, pH=7.4, that included 0.01 M 3,5-dinitrosalicylic acid, 0.1 M 1-ethyl-3-(3-dimethylamine propyl)carbodiimide (EDC), and 0.1 M N-hydroxysulfosuccinimide sodium salt. The capillaries were allowed to react with this solution for 2 hours. The resulting capillaries were washed with a 0.01 M phosphate buffer solution, pH=7.4, and dried.

(b) The base of a vial, 0.5 cm diameter, 1.0 cm height, were coated with a gold layer by vacuum deposition. The gold surface was modified by the 3,5-dinitrosalicylic acid antigen monolayer by a procedure similar to that described in Example 2 for the assembly of the antigen monolayer on the Au-surfaces associated with the quartz crystal.

5.3 Preparation of Biotinylated DNP-Ab

The DNP-Ab was modified with biotin as described in Example 3.7.1.

5.4 Analysis of 2.4-DNT by the Competition Method and Filtering Support Cartridge 10 µl of a diluted 2,4-DNT solution, that included 0.156 ng of 2,4 DNT were added to 10 µl of a $4.2 \times 10^{-8}$ M biotinylated DNP-Ab solution (DNP-Ab-B). The mixture was incubated for 10 mins. and then introduced into the modified glass capillary. The solution was incubated in the glass capillary for an additional 10 mins. The solution from the capillary was then injected into the measuring cell, and the time-dependent frequency changes of the crystal was recorded.

As a reference system that lacks the DNT-analyte, 10 µl of the $4.2 \times 10^{-8}$ M DNP-Ab-B probe solution, and the resulting mixture was treated in the capillary filtering column and injected into the cell in the same manner as above.

Figure 32:
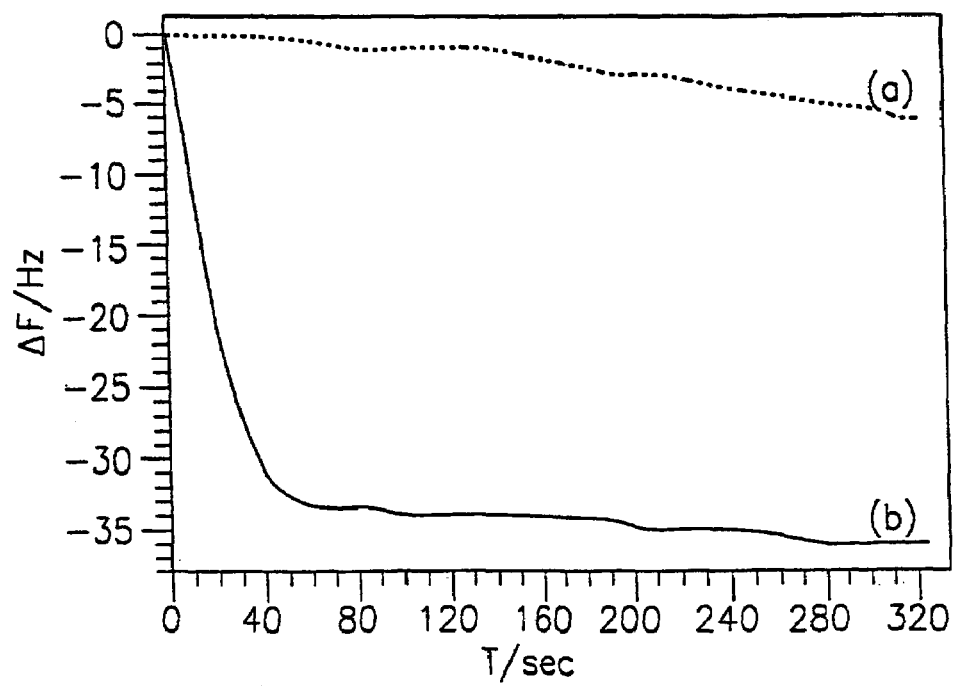
FIG. 32 shows a change in the resonance frequency (T/sec denotes Time in seconds) of the crystal of FIG. 31 upon exposure of the sensing surface to a reference system (curve a, no analyte) in the case of a sample containing 2,4-DNT (curve b).

FIG. 32 (curve a), shows the crystal frequency change upon injection of the reference system. No significant frequency changes was observed ($\Delta f < -5.0$ Hz), implying that no DNP-Ab-B associated to the biotin/avidin monolayer-modified crystal. The results indicate that the DNP-Ab-B is filtered by the antigen-modified capillary. FIG. 32 (curve b), shows the frequency changes of the same crystal upon injection of the 2,4-DNT analyte sample. A frequency decrease of $\Delta f = -35$ Hz is observed, indicating that the antigen-occupied DNP-Ab passes through the filtering column and associates to the biotin-avidin monolayer.

6. Analysis of DNT/TNT by the Enzyme Embodiment

Figure 33:
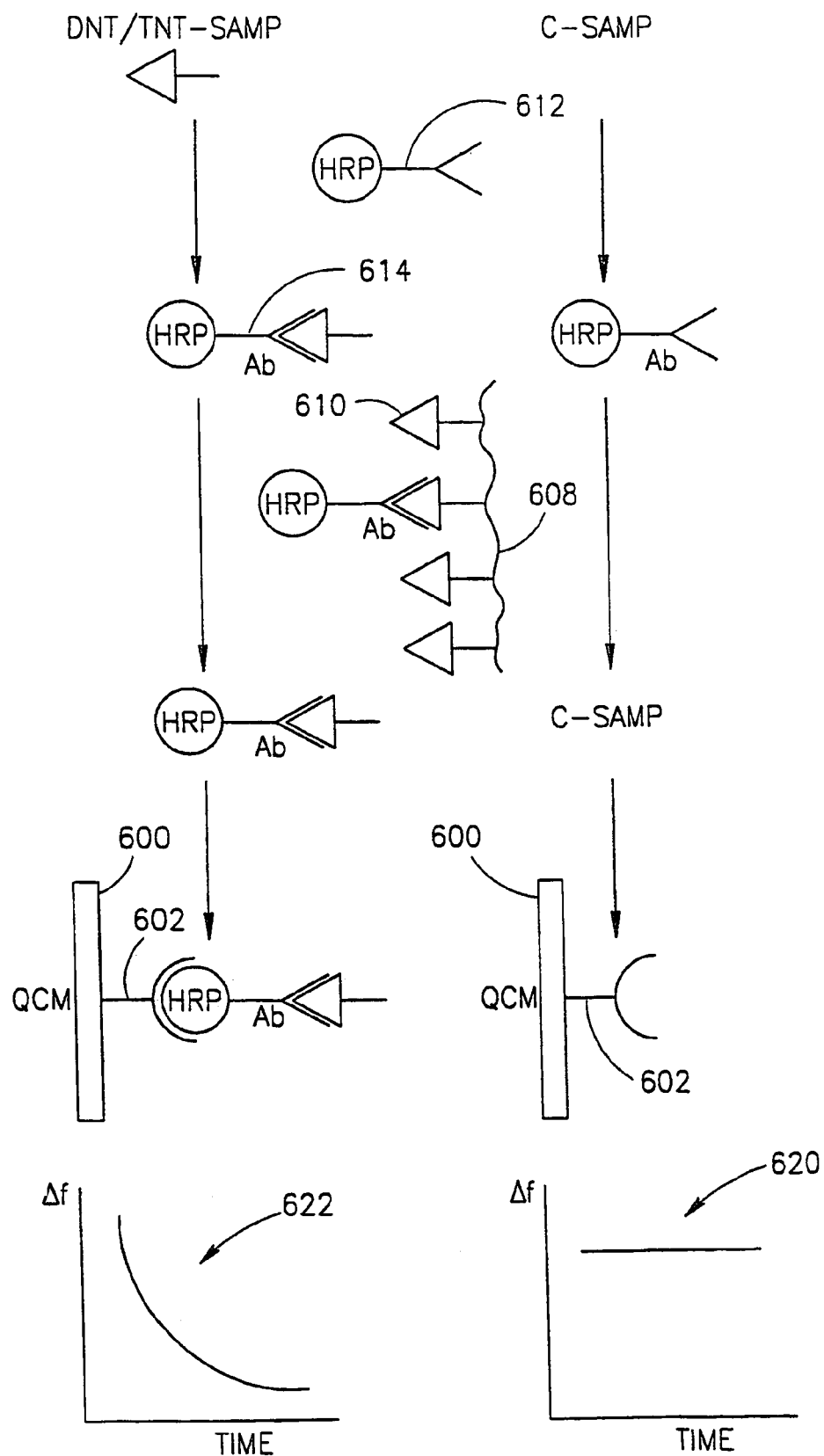
FIGS. 33 and 34 are schematic illustrations of the enzyme embodiment DNT/TNT-SAMP denoting a sample containing DNT and TNT, C-SAMP denoting a clean sample, SUB denoting substrate and PROD denoting product).
Figure 34:
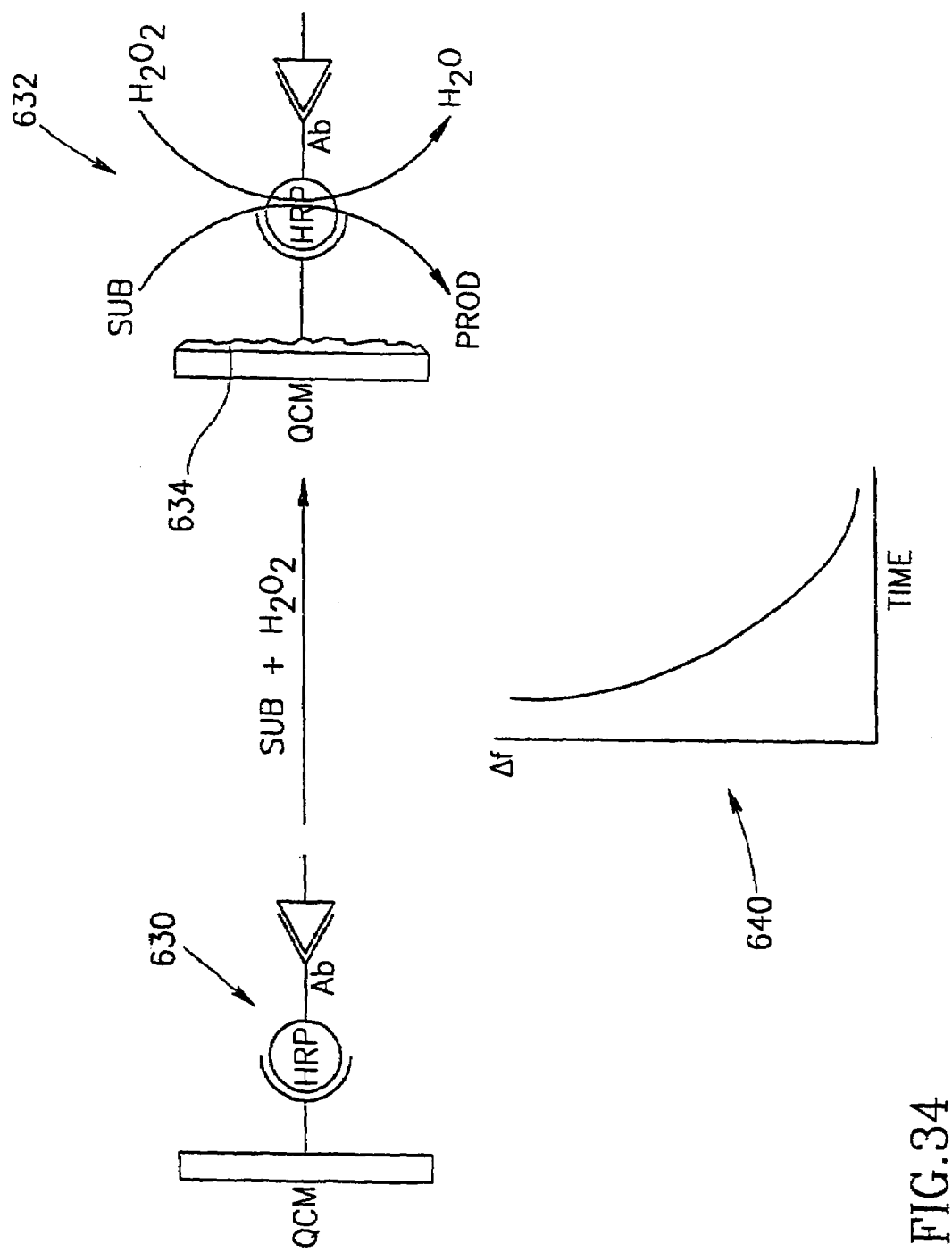

This embodiment is essentially a modification of the basic filtration embodiment described in Example 5 and is outlined in FIGS. 33 and 34.

The electrode on the quartz crystal 600 is modified by anti-horseradish peroxidase antibody (anti-HRP) 602 to generate the sensing surface for HRP-Ab conjugate 604. A filtering support 608 may be a solid matrix, a filtering material, to which antigen 610 is linked.

The probing antibody is modified by HRP to yield a HRP-Ab conjugate 612. The HRP-Ab conjugate 612 is solubilized in an aqueous solution yielding the probe solution.

For analysis, a sample is first interacted with the HRP-Ab probe solution and incubated for a time sufficient to allow binding of the antibody to explosive molecules in the sample (if any). The probe solution is then passed through or interacted with the filtering support 608 and subsequently introduced into the measuring cell and allowed to interact with the modified quartz crystal. The case of a clean sample is illustrated on the right-hand side of FIG. 33, while the case of a DNT/TNT-contaminated sample is illustrated on the left-hand side of FIG. 33. A clean sample lacking DNT or TNT, will result in the association of the probe HRP-Ab to the filtering support 608 (due to the bioaffinity interaction between the antigen associated with the filtering support (an antibody that is part of the HRP-Ab conjugate). The resulting solution introduced to the cell will lack the HRP-Ab and the crystal's mass will thus not change. Consequently, there will be no resonance frequency change (see illustrative graph 620).

A positive DNT/TNT sample will result in binding of the antigen to the antibody to yield conjugate 614 in the probe solution. The filtering support will not bind the HRP-Ab since it is associated with the DNT/TNT antigen. Interacting the probe solution with the crystal will then result in association of the HRP-Ab conjugate 614 to the anti-HRP monolayer (due to the bioaffinity interaction between anti-HRP on the surface and HRP that is part of the HRP-Ab conjugate). This results in a frequency decrease of the crystal (see illustrative graph 622).

When the crystal carrying the anti-HRP/HRP-Ab/TNT complex 630 is incubated in a solution of hydrogen peroxide and 4-chloronaphthol, the HRP catalyzes a reaction 632 in which this substrate (4-chloronaphthol) is oxidized by the hydrogen peroxide giving rise to an insoluble product which forms a precipitate 634 on the electrode's surface. The formation of the insoluble product decreases dramatically the frequency of the crystal (see illustrative graph 640 in FIG. 34) that results in a significant amplification of the primary signal.

The specific biocatalytic reaction, in addition to amplifying the primary signal, serves also as a confirmation to verify the primary signal. In the case of non-specific adsorption of some impurities, the secondary amplified signal will not arise. Thus, the secondary decrease in the crystal's frequency that is biocatalyzed by the enzyme (in a specific example—HRP) can serve as the confirmation of the bioaffinity coupling of the HRP-Ab conjugate to the crystal's surface. A wrong primary frequency change resulting from absorption of non-catalytic active species can thus be easily discriminated. The amount of the precipitate, and hence the extent of the signal amplification, may be controlled by either the surface concentration of the HRP and by the time of the crystal incubation in the developing solution which contains hydrogen peroxide and 4-chloronaphthol. It is clear that the extent of amplification can thus be easily controlled by any one of the incubation times, e.g. the time in which the HRP is permitted to catalyze the developing reaction.

Many different enzymes and respective substrates which produce insoluble products may be used in this embodiment. The following are some examples:

i. Horseradish peroxidase (HRP) or microperoxidase-11, with several substrates including 4-chloronaphthol, 3,3'-diaminobenzidine tetrahydro-chloride, or 3-amino-9-ethyl carbazol.

ii. Alkaline phosphatase with the substrates: 5-bromo-4-chloro-3'-indolyphosphate p-toluidine or nitro-blue tetrazolium chloride.

iii. Glucose oxidase with the substrates: nitro-blue tetrazolium chloride, tetranitroblue tetrazolium.

iv. Galactosidase with the substrate: 5-bromo-4-chloro-D-galactopyranoside.

Obviously, as will be appreciated, in each case the surface of the electrode should carry the respective anti-enzyme antibody.

---

The invention claimed is:

1. An isolated antibody or antibody fragment, comprising heavy and light chain variable region sequences of SEQ ID Nos: 6 and 8.

2. The isolated antibody or antibody fragment of claim 1, which is selected from the group consisting of monoclonal antibodies, IgM antibodies, IgG antibodies, an antibody without the Fc region, and a single chain antibody.

3. The isolated antibody or antibody fragment of claim 1, which is a monoclonal antibody.

4. Apparatus for detecting small assayed molecules in a sample, comprising:
   (a) a sensing member comprising a piezoelectric crystal having at least one sensing surface which can interact with a medium in contact therewith by either binding a first indicator agent from the medium, or by releasing a second indicator agent originally immobilized on the sensing surface into the medium;
   the medium being either the sample, in which case the assayed molecule present causes the release of the second indicator agent from the at least one sensing surface, or a treated sample preparation obtained by reacting the sample with one or both of a reagent solution or sample-processing hardware, such that said medium comprises a first indicator agent or a second indicator agent-releasing species at a concentration of said agent or species which is in correlation to the concentration of the assayed molecule in the sample, the binding or release resulting in a change of mass of the sensing surface, wherein:
   said at least one sensing surface carries capturing agents which bind to neutralizing agents at an assayed molecule-binding domain of the neutralizing agent;
   said capturing agents are assayed molecules, residues or moieties and said neutralizing agents comprise first antibodies which bind to the assayed molecules; and
   said first antibodies are a plurality of an antibody or antibody fragment that comprises heavy and light chain variable region sequences of SEQ ID NOs: 6 and 8;
   (b) a testing cell for holding said medium and bringing it into contact with said at least one sensing surface; and
   (c) an electric or electronic utility for inducing vibrations in the piezoelectric crystal and measuring resonance frequency thereof, a change in resonance frequency after contact between the sensing surface and the medium, indicating presence of the assayed molecules in the sample.

5. An apparatus according to claim 4, wherein the degree of change in resonance frequency serves as a measure of the level of said assayed molecule in said sample.

6. An apparatus according to claim 4, wherein said assayed molecule is an explosive molecule.

7. An apparatus according to claim 4, whereins said first antibodies are monoclonal antibodies.

8. An apparatus according to claim 4, wherein said at least one sensing surface carries residues or moieties of the assayed molecules bound to said first antibodies which can competitively bind to soluble assayed molecules in a medium in contact with the at least one sensing surface, whereby in the presence of the assayed molecules in said medium the first antibodies are released from the at least one sensing surface.

9. An apparatus according to claim 8, wherein the first antibodies are bound or complexed to a mass-increasing agent.

10. An apparatus according to claim 9, wherein said mass increasing agent comprises a second antibody which binds to said first antibody, or comprises avidin or streptavidin bound to a biotin residue conjugated to the first antibody.

11. An apparatus according to claim 4, wherein said assay molecule is DNT or TNT.

12. A system for detecting small assayed molecules in a sample comprising an apparatus according to claim 4 and one or both of reagents and hardware for processing said sample or for introducing it into said cell.

13. A system according to claim 12, wherein said hardware comprises a flow system for propelling a medium comprising the sample into said cell.

14. A system according comprising:
   (a) a sensing member comprising a piezoelectric crystal having at least one sensing surface which carries residues or moieties of said assayed molecules bound to a first antibody or antibody fragment that comprises heavy and light chain variable region sequences of SEQ ID Nos:6 and 8;
   (b) a testing cell for holding a medium and bringing it into contact with said at least one sensing surface, whereby in the presence of the assayed molecules in the medium, at least some of a plurality of said first antibody or antibody fragment are released into the medium;
   (c) hardware for introducing the sample into the testing vessel; and
   (d) an electric or electronic utility for inducing vibrations in the piezoelectric crystal and measuring resonance frequency thereof, a reduction in resonance frequency after contact between the sensing surface and the medium, indicating presence of said assayed molecule in the sample.

15. A system according to claim 14, wherein said assayed molecule is an explosive molecule.

16. A system according to claim 15, wherein the assayed molecule is DNT or TNT.

17. A system according to claim 14, wherein said first antibody or antibody fragment is bound to a mass-increasing agent.

18. A system according to claim 17, wherein said mass increasing agent comprises a second antibody, or avidin or a streptavidin which bind to a biotin moiety conjugated to said first antibody or antibody fragment.

19. A system comprising:
(a) a sensing member comprising a piezoelectric crystal having at least one sensing surface which carries residues or moieties of the assayed molecules;
(b) a reagent system comprising a first antibody or antibody fragment that comprises heavy and light chain variable region sequences of SEQ ID NOs: 6 and 8;
(c) a testing cell for holding a medium and bringing it into contact with said at least one sensing surface, whereby in the presence of the assayed molecules in the medium, at least some of a plurality of said first antibody or antibody fragment are released into the medium;
(d) an arrangement for contacting the sample with said reagent system to obtain a treated sample preparation and for introducing the treated sample preparation into the testing vessel; and
(e) an electric or electronic utility for inducing vibrations in the piezoelectric crystal and measuring resonance frequency thereof, a decrease in resonance frequency after contact between the sensing surface and the treated sample preparation, indicating that the sample is free of the assayed molecules.

20. A system according to claim 19, wherein the assayed molecule is an explosive molecule.

21. A system according to claim 20, wherein the assayed molecule is DNT or TNT.

22. A system according to claim 19, comprising a mass-increasing agent for binding to said first antibody or antibody fragment.

23. A system according to claim 22, wherein said mass increasing agent comprises a second antibody, or avidin or streptavidin which bind to a biotin moiety conjugated to said first antibody or antibody fragment.

24. A system comprising:
(a) a sensing member comprising a piezoelectric crystal having at least one sensing surface which carries capturing agents for binding to an antibody or antibody fragment that comprises heavy and light chain variable region sequences of SEQ ID NOs: 6 and 8;
(b) a testing cell for holding a medium and bringing it into contact with said at least one sensing surface;
(c) a reagent system comprising said antibody or antibody fragment which can bind to the assayed molecules;
(d) an arrangement for contacting the sample with the reagent system under condition and for a time permitting binding of said antibody or antibody fragment to the assayed molecules, to obtain a treated sample preparation;
(e) a filtration system for filtering out from said treated sample preparation of said antibody or antibody fragment unbound to an explosive molecule to obtain a filtrate essentially devoid of such unbound antibody or antibody fragment;
(f) arrangement for transfer of said filtrate to said testing cell; and
(g) an electric or electronic utility for inducing vibrations in the piezoelectric crystal and measuring resonance frequency thereof, an increase in resonance frequency after contact between the sensing surface and the filtrate, indicating presence of the assayed molecules in the sample.

25. A system according to claim 24, wherein the assayed molecule is an explosion molecule.

26. A system according to claim 25, wherein the assayed molecule is DNT or TNT.

27. A system according to claim 24, wherein said filtration system comprises immobilized residues or moieties of molecules of the assayed molecule.

28. A system according to claim 24, wherein said antibody or antibody fragment is conjugated to a moiety which binds to said capturing agents.

29. A system according to claim 28, wherein said moiety is a biotin residue and said capturing agent is avidin or streptavidin.

30. A system comprising:
(a) a sensing member comprising a piezoelectric crystal having at least one sensing surface which carries capturing agents for binding to an antibody or antibody fragment that comprises heavy and light chain variable region sequences of SEQ ID NOs: 6 and 8;
(b) a testing cell for holding a medium and bringing it into contact with said at least one sensing surface;
(c) a reagent system comprising said antibody or antibody fragment which can bind to the assayed molecules, said antibody or antibody fragment being conjugated to an enzyme which can catalyze a reaction yielding an insoluble reaction product;
(d) an arrangement for contacting the sample with the reagent system under conditions and for a time permitting binding of said antibody or antibody fragment to the assayed molecules, to obtain a treated sample preparation;
(e) a filtration system for filtering out from said treated sample preparation said antibody or antibody fragment unbound to an assayed molecule to obtain a filtrate essentially devoid of such unbound antibody or antibody fragment;
(f) arrangement for transfer of said filtrate to said testing cell;
(g) an ensemble of reagents and conditions for inducing said enzyme to catalyze the reaction yielding the insoluble reaction product; and
(h) an electric or electronic utility for inducing vibrations in the piezoelectric crystal and measuring resonance frequency thereof, an increase in resonance frequency after contact between the sensing surface and the filtrate or after permitting the enzyme to catalyze said reaction, indicating presence of the assayed molecule in the sample.

31. A system according to claim 30, wherein the assayed molecule is an explosive molecule.

32. A system according to claim 31, wherein the assayed molecule is DNT or TNT.

33. A system according to claim 31, wherein said filtration system comprises immobilized residues or moieties of the assayed molecules.

34. A system according to claims 31, wherein said capturing agent is an immobilized antibody which binds a moiety of said enzyme, such binding not interfering with the catalytic activity of said enzyme.

35. A system according to claims 30, wherein said enzyme is selected from the group consisting of horseradish peroxidase, microperoxidase, alkaline phosphatasae, glucoseoxidase and galactosidase.

36. A method for detecting a small assayed molecule in a sample, comprising:
  (a) providing a sensing member comprising a piezoelectric crystal having at least one sensing surface which can interact with a medium in contact therewith by either binding a first indicator agent from the medium, or by releasing a second indicator agent originally immobilized on the sensing surface into the medium, said at least one sensing surface carries residues and moieties of the assayed molecule bound to a first antibody or antibody fragment that comprises heavy and light chain variable region sequences of SEQ ID NOs: 6 and 8;
  (b) contacting the at least one sensing surface with a medium being either the sample in which case the assayed molecule if present causes the release of the second indicator agent from the sensing surface, or being a treated sample preparation obtained by reacting the sample with one or both of a reagent solution or sample-processing hardware, such that said medium comprises a first indicator agent or a second indicator agent-releasing species, at a concentration of said agent or species which is in correlation to the concentration of the assayed molecule in the sample, the binding or release resulting in a change of mass of the sensing surface;
  (c) inducing vibrations in the piezoelectric crystal and measuring resonance frequency thereof; and
  (d) determining whether a change in resonance frequency after contact between the sensing surface and the medium occurred, such change indicating presence of the assayed molecule in the sample.

37. A method according to claim 36, wherein said small molecule is an explosive.

38. A method according to claim 37, wherein said explosive is DNT or TNT.

39. A method according to claim 36, wherein the degree of change in resonance frequency serves as a measure of the level of said molecule in said sample.

40. A method comprising:
  (a) providing a sensing member comprising a piezoelectric crystal having at least one sensing surface which carries residues or moieties of the assayed molecule bound to a first antibody or antibody fragment that comprises heavy and light chain variable region sequences of SEQ ID NOs: 6 and 8;
  (b) contacting the sample with the at least one sensing surface;
  (c) inducing vibrations in the piezoelectric crystal and measuring resonance frequency thereof; and
  (d) determining whether there occurred an increase in resonance frequency after contact between the sensing surface and the medium, such increase indicating presence of the assayed molecule in the sample.

41. A method according to claim 40, wherein the assayed molecules are explosive molecules.

42. A method according to claim 41, wherein the assayed molecule is DNT or TNT.

43. A method according to claim 40, comprising binding a mass increasing agent to said first antibody or antibody fragment.

44. A method according to claim 43, wherein said mass increasing agent comprises a second antibody, or an avidin or a streptavidin molecule which binds to a biotin moiety conjugated to said first antibody or antibody fragment.

45. A method according comprising:
  (a) providing a sensing member comprising a piezoelectric crystal having at least one sensing surface which carries residues or moieties of the assayed molecules;
  (b) contacting the sample with a protein molecule which has the binding characteristics of said first antibody or antibody fragment and incubating for a time allowing said first antibody or antibody fragment to bind to the assayed molecules if present in the sample, to yield a treated sample preparation;
  (c) contacting the treated sample preparation with the at least one sensing surface;
  (d) inducing vibrations in the piezoelectric crystal and measuring resonance frequency thereof; and
  (e) determining whether there occurred a decrease in resonance frequency after contact between the sensing surface and the treated sample preparation, such decrease indicating presence of the assayed molecule in the sample.

46. A method according to claim 45, wherein the assayed molecule is an explosive molecule.

47. A method according to claim 46 wherein the assayed molecule is DNT or TNT.

48. A method according to claim 45, comprising binding a mass-increasing antibody to said first antibody or antibody fragment.

49. A method according to claim 48, wherein said mass increasing agent comprises a second antibody, or an avidin or a streptavidin molecule which binds to a biotin moiety conjugated to said first antibody or antibody fragment.

50. A method comprising:
  (a) providing a sensing member comprising a piezoelectric crystal having at least one sensing surface which carries capturing agents for binding to a first antibody or antibody fragment that comprises heavy and light chain variable region sequences of SEQ ID NOs: 6 and 8;
  (b) contacting the sample with said first antibody or antibody fragment which can bind to the assayed molecules under conditions and for a time permitting binding of said first antibody or antibody fragment to the assayed molecules, to obtain a treated sample preparation;
  (c) filtering the treated sample preparation through filtration system to filter out said first antibody or antibody fragment unbound to the assayed molecules to obtain a filtrate essentially devoid of such unbound first antibody or antibody fragment
  (d) contacting said filtrate with the at least one sensing surface;
  (e) inducing vibrations in the piezoelectric crystal and measuring resonance frequency thereof; and
  (f) determining whether there occurred a increase in resonance frequency after contact between the sensing surface and the treated sample preparation, such increase indicating presence of the assayed molecules in the sample.

51. A method according to claim 50, wherein the assayed molecules are explosive molecules.

52. A method according to claim 51, wherein the assayed molecule is DNT or TNT.

53. A method according to claim 50, wherein said filtration system comprises immobilized residues or moieties of the assayed molecules.

54. A method according to claim 50, wherein said first antibody or antibody fragment is conjugated to a moiety which binds to said capturing agents.

55. A method according to claim 54, wherein said moiety is a biotin residue and said capturing agent is avidin or streptavidin.

56. A method comprising:
(a) providing sensing member comprising a piezoelectric crystal having at least one sensing surface which carries capturing agents for binding to a first antibody or antibody fragment that comprises heavy and light chain variable region sequences of SEQ ID NOs: 6 and 8;
(b) contacting the sample with said first antibody or antibody fragment which can bind to the assayed molecules, said protein molecule being conjugated to an enzyme which can catalyze a reaction yielding an insoluble reaction product, for a time permitting binding of said first antibody or antibody fragment to the assayed molecules, to obtain a treated sample preparation;
(c) filtering the treated sample preparation through filtration system to filter out said first antibody or antibody fragment unbound to the assayed molecules to obtain a filtrate essentially devoid of such unbound first antibody or antibody fragment
(d) contacting said filtrate with the at least one sensing surface;
(e) applying condition permitting the enzyme to catalyze the production of the insoluble reaction product;
(f) inducing vibrations in the piezoelectric crystal and measuring resonance frequency thereof; and
(g) determining whether there occurred a decrease in resonance frequency after contact between the sensing surface and said filtrate or after application of said conditions, such decrease indicating presence of the assayed molecules in the sample.

57. A method according to claim 56 wherein the assayed molecule is an explosive molecule.

58. A method according to claim 57, wherein the assayed molecule is DNT or TNT.

59. A method according to claim 57, wherein said filtration system comprises immobilized residues or moieties of said assayed molecule.

60. A method according to claim 57, wherein said capturing agent is an immobilized antibody which binds a moiety of said enzyme, such binding not interfering with the catalytic activity of said enzyme.

61. A method according to claim 57, wherein said enzyme is selected from the group consisting of horseradish peroxidase, microperoxidase, alkaline phosphatase, glucoseoxidase and galactosidase.

* * * * *